(12) United States Patent
Johnson et al.

(10) Patent No.: US 8,890,059 B2
(45) Date of Patent: Nov. 18, 2014

(54) USE OF CRYOGENIC ION CHEMISTRY TO ADD A STRUCTURAL CHARACTERIZATION CAPABILITY TO MASS SPECTROMETRY THROUGH LINEAR ACTION SPECTROSCOPY

(75) Inventors: Mark A. Johnson, Woodbridge, CT (US); Michael Z. Kamrath, Hutchinson, MN (US); Etienne Garand, New Haven, CT (US)

(73) Assignee: Yale University, New Haven, CT (US)

( * ) Notice: Subject to any disclaimer, the term of this patent is extended or adjusted under 35 U.S.C. 154(b) by 35 days.

(21) Appl. No.: 13/878,892

(22) PCT Filed: Oct. 11, 2011

(86) PCT No.: PCT/US2011/055681
§ 371 (c)(1),
(2), (4) Date: May 28, 2013

(87) PCT Pub. No.: WO2012/051138
PCT Pub. Date: Apr. 19, 2012

(65) Prior Publication Data
US 2014/0145073 A1    May 29, 2014

Related U.S. Application Data

(60) Provisional application No. 61/391,877, filed on Oct. 11, 2010.

(51) Int. Cl.
| | | |
|---|---|---|
| *H01J 3/00* | (2006.01) | |
| *H01J 49/26* | (2006.01) | |
| *B01D 59/44* | (2006.01) | |
| *H01J 49/42* | (2006.01) | |
| *H01J 49/10* | (2006.01) | |
| *G01N 21/31* | (2006.01) | |
| *H01J 49/00* | (2006.01) | |
| *G01J 3/42* | (2006.01) | |
| *G01N 21/35* | (2014.01) | |
| *G01N 21/33* | (2006.01) | |

(52) U.S. Cl.
CPC ............... *G01J 3/42* (2013.01); *H01J 49/424* (2013.01); *H01J 49/10* (2013.01); *G01N 21/31* (2013.01); *G01N 21/33* (2013.01); *H01J 49/0031* (2013.01); *G01N 21/3504* (2013.01)
USPC ............ 250/282; 250/292; 250/288; 250/281

(58) Field of Classification Search
CPC .. H01J 49/0481; H01J 49/424; G01N 27/622; G01N 21/3504
USPC .................................. 250/282, 292, 288, 281
See application file for complete search history.

(56) References Cited

U.S. PATENT DOCUMENTS

| | | | |
|---|---|---|---|
| 7,476,853 B2 * | 1/2009 | Zubarev et al. | 250/292 |
| 7,923,681 B2 * | 4/2011 | Collings et al. | 250/282 |

(Continued)

OTHER PUBLICATIONS

Williams DH, Bardsley B. Angew Chem Int Edit, 1999;38:1173-1193.

(Continued)

*Primary Examiner* — Nikita Wells
(74) *Attorney, Agent, or Firm* — Henry D. Coleman; R. Neil Sudol

(57) ABSTRACT

The present invention relates to mass spectrometry and infrared spectrometry and in particular, to a method of providing highly resolved infrared spectra of mass-selected, complex (e.g., biopolymer, polypeptide, organic chemical, an organometallic compound, a carbohydrate, a polynucleotide or oligonucleotide compound) ions to be obtained in a general fashion.

23 Claims, 18 Drawing Sheets

(56) References Cited

U.S. PATENT DOCUMENTS

| | | | |
|---|---|---|---|
| 8,198,583 B2 * | 6/2012 | Brekenfeld et al. | 250/282 |
| 8,642,948 B2 * | 2/2014 | Makarov et al. | 250/283 |

OTHER PUBLICATIONS

Gustafson JL, Lim D, Miller SJ. Science, 2010;328:1251-1255.
Taylor MS, Jacobsen EN. Angew Chem Int Edit, 2006;45:1520-1543.
Jacobsen EN, Doyle AG. Chem Rev, 2007;107:5713-5743.
Bleicher KH, Bohm HJ, Muller K, Alanine AL. Nat Rev Drug Discovery, 2003;2:369-378.
Bajorath F. Nat Rev Drug Discovery, 2002;1:882-894.
Jorgensen WL. Science, 2004;303:1813-1818.
Shoichet BK. Nature, 2004;432:862-865.
Prins LJ, Reinhoudt DN, Timmerman P. Angew Chem Int Edit, 2001;40:2382-2426.
Ham S, Cha S, Choi JH, Cho M. J Chem Phys, 2003;119:1451-1461.
Perrin CL, Nielson JB. Annu Rev Phys Chem, 1997I48L511-544.
Kamrath MZ, Relph RA, Guasco TI, Leavitt CM, Johnson MA. Int J Mass Spec, 2011;300:91-98.
Kamrath MZ, Garand E, Jordan PA, Leavitt CM, Wolk AB, Van Stipdonk MJ, Miller SJ, Johnsonma. J Am Chem Soc, 2011;133:6440-6448.
Okumura M, Yeh LI, Myers JD, Lee YT. J Chem Phys, 1986;85:2328-2329.
Stearns JA, Mercier S, Seaiby C, Guidi M, Boyarkin OV, Rizzo TR. J Am Chem Soc, 2007;129:11814-11820.
Goebbert DJ, Wende T, Bergmann R, Meijer G, Asmis KR. J Phys Chem A, 2009;113:5674-5880.
Fenn JB, Mann M, Meng CK, Wong SF, Whitehouse CM. Science, 1989;246:64-71.
Stepanian SG, Reva ID, Radchenko ED, Sheina GG. Vib Spectrosc, 1996;11:123-133.
Ishiuchi S, Shitomi H, Takazawa K, Fujii M. Chem Phys Lett, 1998;283:243-250.
Tadesse L, Nazarbaghi R, Walters L. J Am Chem Soc, 1991;113:7036-7037.
Haris PI, Robillard GT, Vandijk AA, Chapman D. Biochemistry, 1992;31:6279-6284.
Sonar S, Lee CP, Coleman M, Patel N, Liu XM, Marti T, Khorana HG, Rajbhandary UL, Rothschild KJ. Nat Struct Biol, 1994;1:512-517.
Lin YS, Shorb JM, Mukherjee P, Zanni MT, Skinney JL. J Phys Chem B, 2009;113:592-602.
Arkin IT, Torres J, Adams PD. J Mol Biol, 2000;300:677-685.
Ohanessian G, Semrouni D, Balaj OP, Calvo F, Correia CF, Clavaguera CJ. Am Soc Mass Spectrom, 2010;21:728-738.
Dungar RC, Steill JD, Oomens J. Int J Mass Spectrom, 2010;297:107-115.
Bakker JM, Mac Aleese L, Von Helden G, Meijer G. J Chem Phys, 2003;119:11180-11185.
Inokuchi Y, Nishi N. J Phys Chem A, 2003;107-11319-11323.
Kim KS, Lee HM, Kumar A, Kolaski M, Kim DY, Lee EC, Min SK, Park M, Choi YC. Physical Chemistry Chemical Physics, 2010;12:6278-6287.
Johnson MA. Vibrational Predissociation Ion Spectroscopy. Encyclopedia of Mass Spectrometry vol. 5, 2002,p. 272-276.
Bush MF, Saykally RJ, Williams ER. Evidence for Water Rings in the Hexahydrated Sulfate Dianion from IR Spectroscopy. J Am Chem Soc, 2007;129:2220-2221.
Rajabi K, Theel K, Gillis EAL, Beran G, Fridgen TD. The Structure of the Protonated Adenine Dimer by Infrared Multiple Photom Dissociation Spectroscopy and Electronic Structure Calculations. J Phys Chem, 2009;113:8099-8107.
Dunbar RC, Moore DT, Oomens J. IR spectroscopic characterization of intermediates in a gas-phase ionic reaction: The decarbonylation of Co+(acetophenone). Int J Mass Spectrom, 2007;265:162-186.

Carl DR, Cooper TE, Oomens J, Steill JD, Armentrout PB. Infrared multiple photom dissociation spectroscopy of cationized methionine: effects of alkali-metal cation size on gas-phase conformation. Phys Chem, 2010;12:3384-3398.
Leavitt CM, Oomens J, Dain RP, Steill J, Groenewold GS, Stipdonk MJV. IRMPD Spectroscopy of Anionic Group II Metal Nitrate Cluster Ions. J Am Soc Mass Spectrom, 2009;20:772-782.
Jiang L, Wende T, Bergmann R, Meijer G, Asmis KR. Gas-Phase Vibrational Spectroscopy of Microhydrated Magnesium Nitrate Ions [MgNO3(H2O)1-4]+. J Am Chem Soc, 2010;132:7398-7404.
Zwier TS. Laser probes of conformational isomerization in flexible molecules and complexes. J Phys Chem, 2006;110:4133-4150.
Okumura M, Yeh LI, Myers JD, Lee YT. Infrared spectra of the cluster ions H7O3+*H2 and H9O4+*H2. J Chem Phys, 1986;85:2328-2329.
Pankewitz T, Lagutsschenkov A, Niedner-Schatteburg G, Xantheas SS, Lee YT. Infrared spectrum of NH4+(H2O): Evidence for mode specific fragmentation. J Chem Phys, 2007;126:074307.
Wild DA, Weiser PS, Bieske EJ, Zehnacker A. The 35Cl—H2 and 35Cl—D2 anion complexes: Infrared spectra and radial intermolecular potentials. J Chem Phys, 2001;115:824-832.
Emmeluth C, Poad BLJ, Thompson CD, Weddle GH, Bieske EJ. Infrared spectra of the Li+*(H2)n (n=1-3) cation complexes. J Chem Phys, 2007;126:204309.
Solca N, Dopfer O. Microsolvation of the Phenol Cation (Ph+) in Nonpolar Environments: Infrared Spectra of Ph+*Ln (L=He, Ne, Ar, N2, CH4). J Phys Chem, 2001;105:5637-5645.
Solca N, Dopfer O. Protonated benzene; IR spectrum and structure of C6H7+. Angew Chem Int Ed, 2002;41:3628-2631.
Carnagie PD, McCoy AB, Duncan MA. IR Spectroscopy and Theory of Cu+(H2O)Ar2 and Cu+(D2O)Ar2 in the O-H (O-D) Stretching Region: Fundamentals and Combination Bands. J Phys Chem, 2009;113:4849-4854.
Douberly GE, Ricks AM, Schleyer PvR, Duncan MA. Infrared spectroscopy of gas phase C3H5+: The allyl and 2-propenyl cations. J Phys Chem, 2008;128:021101-021104.
Fujii A, Sawamura T, Tanabe S, Ebata T, Mikami N. Infrared Dissociation Spectroscopy of the OH Stretching Vibration of Phenol Rare-Gas Van-der-Waals Cluster Ions. Chem Phys Lett, 1994;225:104-107.
Fujii A, Fujimaki E, Ebata T, Mikami N. Infrared spectroscopy of CH stretching vibrations of jet-cooled alkylbenze cations by using the "messenger" technique. J Chem Phys, 2000;112:6275-6284.
Inokuchi Y, Matsushima R, Kobayashi Y, Ebata T. ion core structure in (N2O)n+ (n=2-8) studied by infrared photodissociation spectroscopy. J Chem Phys, 2009;131:044325.
Okumura M, Yeh Li, Myers JD, Lee YT. Infrared-spectra of the solvated hydronium ion-vibrational predissociation spectroscopy of mass-selected H3O+(H2O)N*(H2)M. J Phys Chem, 1990;94:3416-3427.
Vaden TD, Forinash B, Lisy JM. Rotational structure in the asymmetric OH stretch of Cs+*(H2O)*Ar. J Chem Phys, 2002;117:4628-4631.
Miller DJ, Lisy JM. Hydrated Alkali-Metal Cations: Infrared Spectroscopy and ab Initio Calculations of M+(H2O) x=2-5 Ar cluster ions for M=Li, Na, K, and Cs. J Am Chem Soc, 2008;130:15381-15392.
Relph RA, Guasco TL, Elliott BM, Kamrath MZ, McCoy AB, Steele RP, Schofield DP, Jordan KD, Viggiano AA, Ferguson EE, Johnson MA. How the Shape of an H-bonded Network Controls Proton-Coupled Water Activation in HONO formation. Science, 2010;327:308-312.
Schneider H, Vogelhuber KM, Schinle F, Weber JM. Aromatic molecules in anion recognition: Electrostatics versus H-bonding. J Am Chem Soc, 2007;129:13022-13026.
Schneider H, Vogelhuber KM, Weber JM. Infrared spectroscopy of anionic hydrated fluorobenzenes. J Chem Phys, 2007;127:114311.
Pivonka NL, Kaposta C, Brummer M, Von Helden G, Meijer G, Woste L, Neumark DM, Asmis KR. Probing a strong hydrogen bond with infrared spectroscopy: Vibrational predissociation of BrHBr*Ar. J Chem Phys, 2003;118:5275-5278.
Goebbet DJ, Wende T, Bergmann R, Meijer G, Asmis KR. Messenger-Tagging Electrosprayed Ions: Vibrational Spectroscopy of Suberate Dianions. J Phys Chem, 2009;113:5874-5880.

(56) References Cited

OTHER PUBLICATIONS

Wang XB, Wang LS. Development of a low-temperature photoelectron spectroscopy instrument using an electrospray ion source and a cryogenically controlled ion trap. Rev Sci Instrum, 2008;79:073108-073101-073108.

Wang XB, Xing XP, Wang LS. Observation of H2 Aggregation onto a Doubly Charged Anion in a Temperature-Controlled Ion Trap. J Phys Chem, 2008;112:13271-13274.

Headrick JM, Bopp JC, Johnson MA. Predissociation spectroscopy of the argon-solvated H5O2+ "Zundel" cation in the 1000-1900 cm-1 region. J Chem Phys, 2004;121:11523-11526.

Woo HK, Wang XB, Lau KC, Wang LS. Low-Temperature Photoelectron Spectroscopy of Aliphatic Dicarboxylate Monoanions, HO2C(CH2)nCO2- (n=1-10): Hydrogen Bond Induced Cyclization and Strain Energies. J Phys Chem, 2006;110:7801-7805.

Posey LA, Johnson MA. Photochemistry of hydrated electon clusters (H2O)n- (15<n<40) at 1064 nm: Size-dependent competition between photofragmentation and photodetachment. J Chem Phys, 1998;89:4807-4814.

Johnson MA, Lineberger WC. Pulsed Methods for Cluster Ion Spectroscopy, in Techniques for the Study of Ion-Molecule Reactions. Farrar, J.M. and Saunders, W.H., Jr.,(Eds.), Wiley, New York, 1988:591.

O'Connor PB, Costello CE, Earle WE. A high voltage RF oscillator for driving multipole ion guides. J Am Soc Mass Spectrom, 2002;13:1370-1375.

Mathur R, O'Connor PB. Design and implementation of a high power rf oscillator on a printed circuit board for multipole ion guides. Review of Scientific Instruments, 2006;77.

Gerlich D. Ion-Neutral Collisions in a 22-Pole Trap at Very-Low Energies. Phys Scripta, 1995;159:256-263.

Gerlich D. Inhomogenous RF-Fields—A Versatile Tool for the Study of Processes with Slow Ions. Adv Chem Phys, 1992;82:1-176.

Boyarkin OV, Mercier SR, Kamariotis A, Rizzo TR. Electronic Spectrocopy of cold, protonated typtophan and tyrosine. J Am Chem Soc, 2006;128:2816-2817.

41. Gerhards M, Unterberg C, Gerlach A. Structure of a beta-sheet model system in the gas phase: Analysis of the C=O stretching vibrations. Phys Chem Chem Phys, 2002;4:5563-5565.

Stearns JA, Das A, Zwier TS. Hydrogen atom dislocation in the excited state of anthranilic acid: probing the carbonyl stretch fundamental and the effects of water complexation. Phys Chem Chem Phys, 2004;6:2605-2610.

N.S.R.D.N. NIST Computational Chemistry Comparison and Benchmark Database, Release Apr. 15, 2010. Editor: Johnson, RD III, http://cccbdb.nist.gov.

Campognola PJ, Posey LA, Johnson MA. Controlling the internal energy content of size-selected cluster ions: An experimental comparison of the metastable decay rate and photofragmentation methods of quantifying the internal excitations of the (H20)n-. J Chem Phys, 1991;95:7998-8004.

Robertson WH, Kelley JA, Johnson MA. A pulsed supersonic entrainment reactor for the rational preparation of cold ionic complexes. Rev Sci Instrum, 2000;71:4431-4434.

Roscioli JR, McCunn LR, Johnson MA. Quantum Structure of the Intermolecular Proton Bond. Science, 2007;316:249-254.

Yaghmaei S, Khodagholian S, Kaiser JM, Tham FS, Mueller LJ, Morton TH. Chelation of a proton by an aliphatic tertiary diamine. J Am Chem Soc, 2008;130:7836.

Rizzo TR, Stearns JA, Boyarkin OV. Int Rev Phys Chem, 2009;28:481-515.

Olesen SG, Gausco TL, Weddle GH, Hammerum S, Johnson MA. Vibrational predissociated spectra of the Ar-tagged [CH4*H3O+] binary complex: spectroscopic signature of hydrogen bonding to an alkane. Mol Phys, 2010;108:1191-1197.

Duncan MA. Infrared spectroscopy to probe structure and dynamics in metal ion-molecule complexes. Int Rev Phys Chem, 2003;22:407-435.

Tucker TJ, Gai XS, Fenlon EE, Brewer SH, Hochstrasser RM. 2D IR photon echo of Azido- probes for Biomolecular Dynamics. Phys Chem Chem Phys, 2011;13(6):2237-2241.

Wang Y.-S. et al.; Investigations of Protonated and Deprotonated Water Clusters Using a Low-Temperature 22-Pole Ion Trap. J Phys Chem A 2003; 107:4217-4225.

Wang Xue-Bin et al.; Observation of H Aggregation onto a Doubly Charged Anion in a Temperature-Controlled Ion Trap. J Phys Chem A 2008; 112:13271-13274.

* cited by examiner

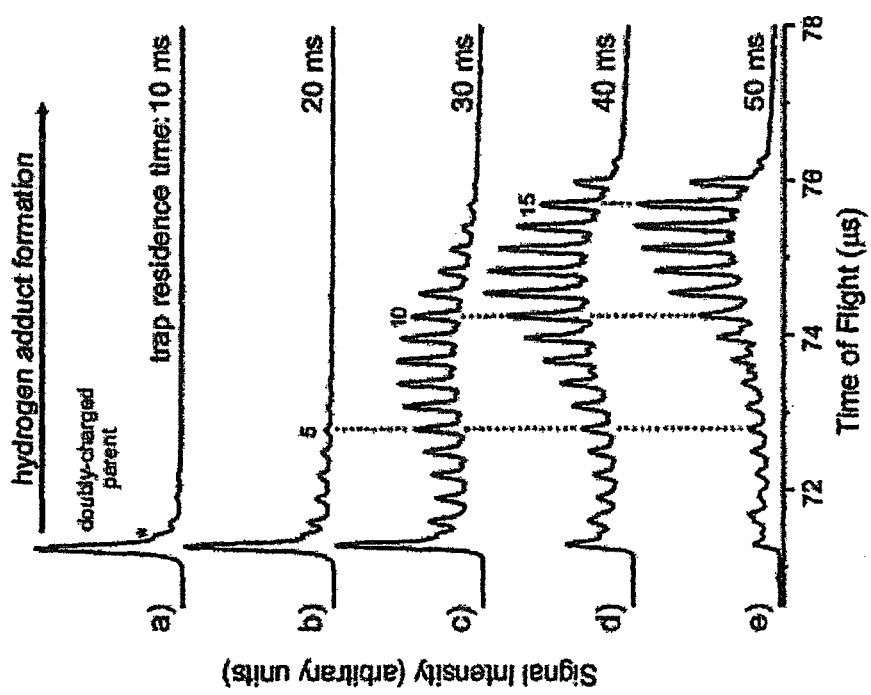

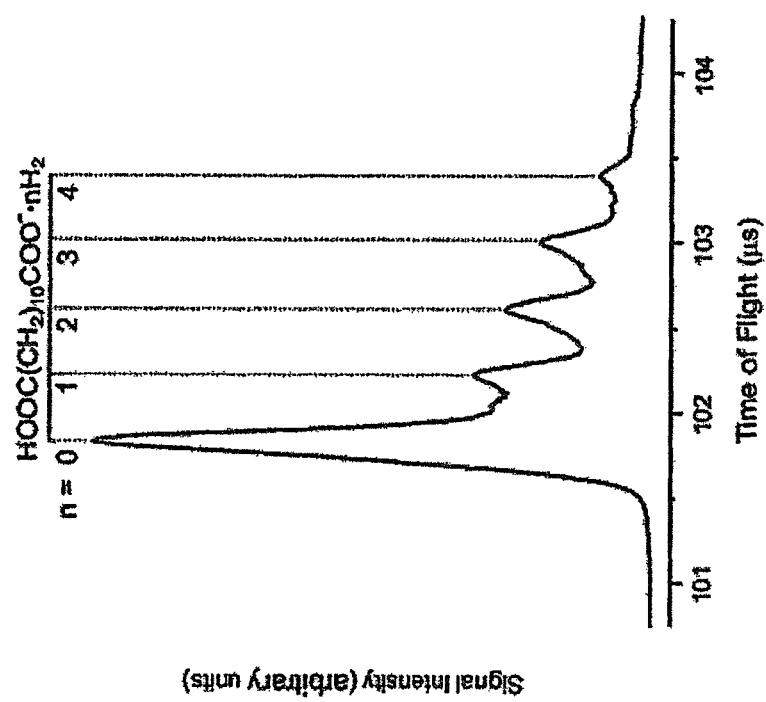

FIGURE 9

Table 1

| Method | Species | Frequencies, cm⁻¹ | | | | |
|---|---|---|---|---|---|---|
| | | $CO_2$ bend | $CO_2$ sym. stretch | $CO_2$ asym. stretch | CH stretches | $H_2$ stretch |
| Experimental | $^-OOC(CH_2)_{10}COO^-\cdot(H_2)_{10}$ | 890 | 1345 | 1611 | 2840, 2853, 2887, 2917, 2929 | 4046 |
| Calculated[a] | $^-OOC(CH_2)_{10}COO^-\cdot(H_2)$ | 840, 844 | 1286, 1289 | 1568, 1571 | 2847, 2850, 2867, 2872, 2896, 2907, 2926 | 3974 |
| | $^-OOC(CH_2)_{10}COO^-$ | 840 | 1286 | 1571 | 2847, 2867, 2871, 2896, 2907, 2926 | N/A |
| | $H_2$ | N/A | N/A | N/A | N/A | 4224 |

[a] Calculated at the B3LYP/6-311++G(d,p) level and scaled by 0.956

Table 2

| Method | Species | Frequencies, cm⁻¹ | | | | | |
|---|---|---|---|---|---|---|---|
| | | $CO_2$ asym. | C=O stretch | shared proton | CH stretches | OH stretch | $H_2$ stretch |
| Experimental | $HOOC(CH_2)_{10}COO^-\cdot(H_2)_2$ | 1608 | 1721 | ~1950 | 2846, 2858, 2889, 2920 | | 4093 |
| Calculated[a] | $HOOC(CH_2)_{10}COO^-$ ring | 1568 | 1673 | 2513 | 2854, 2870, 2876, 1886, 2928, 2933, 2952 | N/A | N/A |
| | $HOOC(CH_2)_{10}COO^-$ chain | 1578 | 1731 | N/A | 2872, 2901, 2911, 2926, 2940 | 3596 | N/A |
| | $H_2$ | N/A | N/A | N/A | N/A | N/A | 4224 |

[a] Calculated at the B3LYP/6-311++G(d,p) level and scaled by 0.956

Scheme 1

Peptidic Host ($h_{H+}$)   Biaryl Guest ($g$)

US 8,890,059 B2

USE OF CRYOGENIC ION CHEMISTRY TO ADD A STRUCTURAL CHARACTERIZATION CAPABILITY TO MASS SPECTROMETRY THROUGH LINEAR ACTION SPECTROSCOPY

This application claims the benefit of priority of International patent application serial no. PCT/US2011/055681, of international filing date 11 Oct. 2011, entitled "Use of Cryogenic Ion Chemistry to add a Structural Characterization Capability to Mass Spectrometry through Linear Action Spectroscopy", which claims the benefit of priority of U.S. provisional application Ser. No. 61/391,877, filed Oct. 11, 2010, entitled "Using cryogenic ion chemistry to add a structure capability to Mass Spectroscopy", the entire contents of said two applications being incorporated by reference herein.

RELATED APPLICATIONS AND GOVERNMENT SUPPORT

This invention was made with government support under FA-9550-091-1-01 39 Air Force Office of Scientific Research. The government has certain rights in the invention.

FIELD OF THE INVENTION

The present invention relates to mass spectrometry and infrared (or Visible/UV) spectrometry and in particular, to a method of providing highly resolved infrared spectra of mass-selected, complex (e.g., biopolymer, polypeptide, organic chemical, an organometallic compound, a carbohydrate, a polynucleotide or oligonucleotide compound) ions to be obtained in a general fashion.

BACKGROUND OF THE INVENTION

Vibrational spectroscopy is emerging as an important tool in the structural characterization of macromolecular ions generated using electrospray ionization (ESI). This is evidenced by the explosion of papers reporting isomer analysis by comparison of vibrational action spectra obtained by infrared multiphoton dissociation (IRMPD) with predictions from electronic structure calculations. [1-6] There are, however, complications in this strategy because the intrinsic non-linearity of the IRMPD method obscures direct comparison with the harmonic absorption spectrum that is readily computed using commercial software packages. [7] Moreover, the fluxional nature of the molecules gives rise to many isomers at low temperature which can often interconvert under ambient conditions.[8] A powerful way to overcome these limitations is through the use of so-called "messenger spectroscopy,"[9, 10] where the ion of interest is complexed with a weakly bound ligand (such as a rare gas atom), and the vibrational action spectrum is monitored by photoinduced loss of the messenger. In this approach, the ion is intrinsically cooled to an upper limit defined by the messenger binding energy, and efficient intramolecular vibrational energy redistribution upon excitation in the fingerprint region of the infrared leads to prompt ejection of the messenger. The resulting action spectra are linear in laser intensity, with a few notable exceptions,[11] and therefore more accurately reflect the linear absorption profiles associated with specific local minimum structures of the target molecule or cluster. This method has been widely used to study ions and ion-solvent clusters that can be prepared using supersonic jet technology.[10, 12-29] On the other hand, application of this method to the classes of ions that can only be generated with ESI is still in its infancy, with a notable recent paper reporting spectra of Kr tagged suberate dianions using a temperature controlled ion trap subsequent to ion generation. [30]

Pursuant to the present invention, the inventors present vibrational predissociation spectra of the anions generated from sequential deprotonation of dodecanedioic acid using $H_2$ as a messenger, where the recent demonstration by Wang and co-workers[31, 32] that large numbers of $H_2$ molecules (up to 12) can be efficiently attached to multiply charged ions from an ESI source using a 10 K radio-frequency (RF) quadrupole ion trap. This is significant because $H_2$ is often non-reactive and quite weakly bound to a variety of closed-shell molecular ions prepared by ESI, and was, in fact, one of the species used in the 1980s for the first reports of the messenger technique.[10, 21, 22] In the case of $H_5O_2^+$, for example, the binding energy and perturbation induced by $H_2$ were on the same order as that found for Ar tagging.[21, 33] In the present invention, the inventors extend the trap-based methods to singly charged anions by pulsing the $H_2$/He mixture into the trap, and report the resulting vibrational spectra of the HOOC$(CH_2)_{10}COO^-$ and $^-OOC(CH_2)_{10}COO^-$ ions over the range 800-4300 $cm^{-1}$. These data are interpreted within the context of a closed, H-bonded ring form for the singly charged species, an arrangement that was inferred by Woo et al.[34] from their analysis of the photoelectron spectra of this species.

BRIEF DESCRIPTION OF THE FIGURES

FIG. 3 shows a mass spectrum demonstrating the effect of trap residence time on $H_2$ tagging efficiency. The doubly charged parent ion ($^-OOC(CH_2)_{10}COO^-$, at left) is observed to accumulate increasing numbers of $H_2$ molecules as the residence time is lengthened from (a) 10 ms to (e) 50 ms.

FIG. 4 shows the mass spectrum of HOOC$(CH_2)_{10}COO^-$·$(H_2)_n$, n=1-4, illustrating the addition of $H_2$ molecules to the singly charged species.

FIG. 9, Tables 1 and 2 show comparison data of the experimental and calculated frequencies which were produced in the experiments conducted and described in the present application. Table 1 shows a comparison of the experimentally measured vibrational transitions of $^-$OOC(CH$_2$)$_{10}$COO$^-$.(H$_2$)$_{10}$ with calculated harmonic frequencies for $^-$OOC(CH$_2$)$_{10}$COO$^-$, $^-$OOC(CH$_2$)$_{10}$COO$^-$.H$_2$ and H$_2$. Table 2 shows a comparison of the experimentally measured vibrational transitions of HOOC(CH$_2$)$_{10}$COO$^-$.(H$_2$)$_2$ with calculated harmonic frequencies of the ring and chain isomers of HOOC(CH$_2$)$_{10}$COO$^-$ and H$_2$.

BRIEF DESCRIPTION OF THE INVENTION

Figure 1:
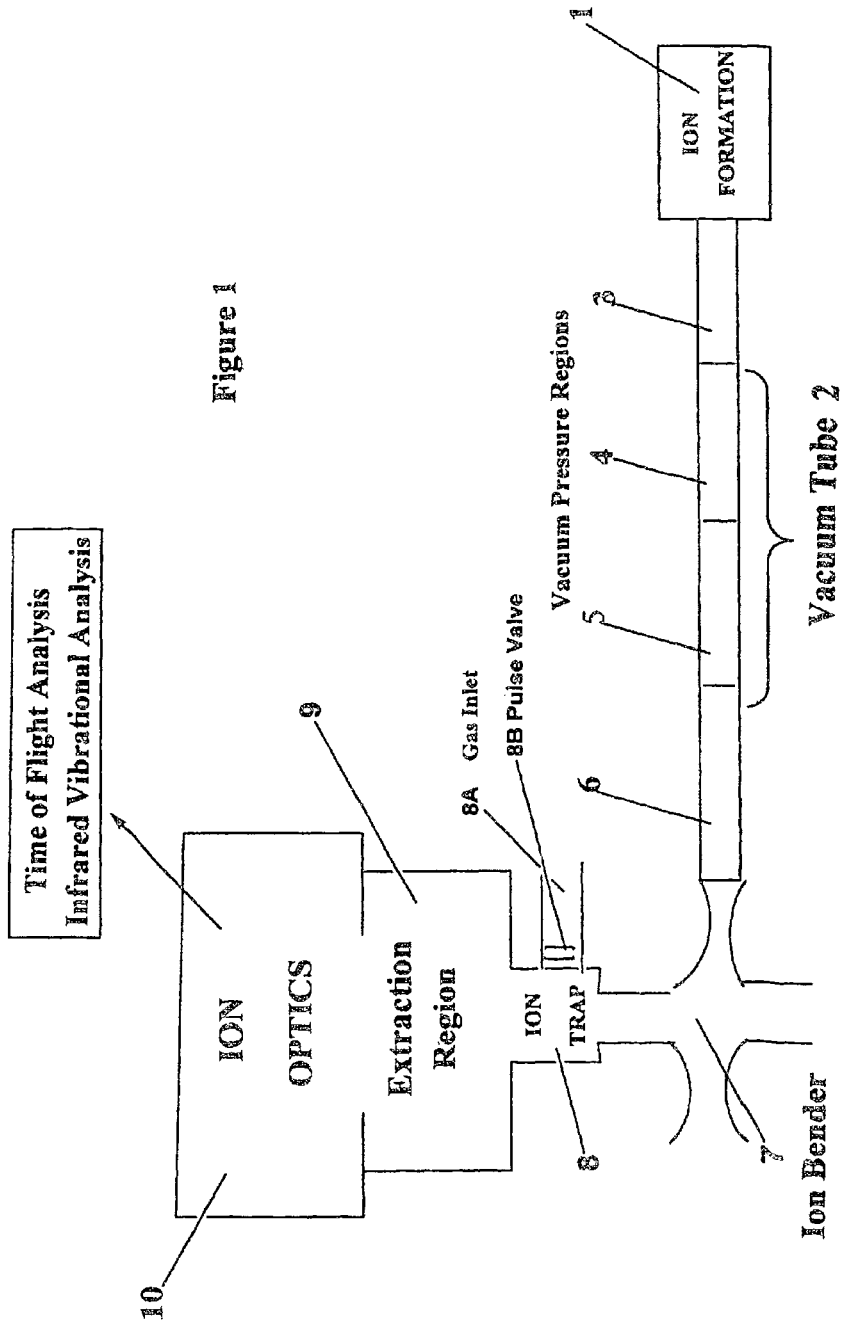
FIG. 1 shows a generalized schematic of the present invention. The various elements presented in FIG. 1 are described in the text of the present application.

The present invention relates to a method of conducting mass spectrometry using weakly attached hydrogen molecules and in particular, to a method of providing highly resolved vibrational and electronic spectra of mass-selected, complex (e.g., biopolymer, proteins, etc.) ions to be obtained in a general fashion. The present invention combines mass spectrometry with infrared spectroscopy to provide infrared spectra which are highly resolved. The present invention relates to the discovery that the formation of adducts between a hydrogen (H$_2$), helium (He), argon (Ar), neon (Ne), krypton (Kr), xenon (Xe), carbon dioxide (CO$_2$), carbon monoxide (CO), nitrogen (N$_2$), methane (CH$_4$), and sulfur hexafluoride (SF$_6$) gas at very low temperatures and selected ions will provide adducts which can be analyzed to provide exceptional infrared resolution of functional group chemistry on the ions.

In particular, the present invention relates to the development of a technique to efficiently produce low temperature hydrogen-, helium-, argon-, neon-, xenon-, krypton-, carbon dioxide-, carbon monoxide-, nitrogen-, methane-, and sulfur hexafluoride-ion complexes or adducts in an ion trap, which are subjected to mass spectrometry and infrared spectroscopy to provide infrared spectra of exceptional functional group resolution. The present invention is therefore directed to the formation of a hydrogen, neon or argon-ion, etc, adduct in an ion trap of a mass spectrometer at very low temperatures (depending upon the gas used range from as low as 5-10 degrees Kelvin for hydrogen to upwards of 50 degrees Kelvin for argon or neon, etc.) wherein ions residing in the ion trap are exposed to a pulsed gas at low temperature in the ion trap for a period effective (generally, less than 1 millisecond to about 100 milliseconds (preferably about 50-95 milliseconds), although this residence time may vary) to allow the gas and ions to complex into a gas-ion adduct or complex. A delay or interval (typically 10 milliseconds to 100 milliseconds, but can be much longer) before the next pulse of gas is then used to allow the pressure inside the trap to return to its original value (ions are released during this period from the ion trap for further processing or analysis) and thus avoid collision-induced dissociation of the cold adducts when they are extracted from the ion trap. Rather routine procedures may be run to determine the optimal pulse rate and pulse interval for each ion and each gas which is used to form the gas-ion adduct. Once formed, the gas-ion adducts are then extracted from the ion trap and sent into a mass spectrometer (to separate the ion-adducts from the non-complexed ions and to identify adduct formation) and subsequently, to an infrared spectrometer in order to provide a photon energy (cm$^{-1}$) spectrum which evidences the various functional groups in the ion to be analyzed (ion of interest).

In a more particular aspect, the present invention is directed to the use of a standard low temperature infrared spectroscopy instrument which analyzes ion complexes of an ion of interest with a gas selected from the group consisting of hydrogen (as a hydrogen/helium mixture), helium (He), argon (Ar), neon (Ne), krypton (Kr), xenon (Xe), carbon dioxide ($CO_2$), carbon monoxide (CO), nitrogen ($N_2$), methane ($CH_4$), and sulfur hexafluoride ($SF_6$) in a low temperature controlled ion trap (generally, at a temperature no higher than about 50 Kelvins, depending upon the complexing gas which is used to form gas-ion adducts which are analyzed) wherein the gas is introduced into the low temperature ion trap (the gas may be introduced at various temperatures ranging from low temperature to room temperature or even higher) by pulsing at intervals ranging from less than about 1 millisecond to about 100 millisecond as otherwise described herein. It has been determined that the introduction of pulsed gas into the ion trap will produce gas-ion adducts (hydrogen-ion, argon-ion or neon-ion, etc) at high efficiency, which are useful for further analysis, in particular, high resolution infrared spectroscopy (e.g. tunable laser, FT-IR, dispersive spectrometers, etc.). In the present invention, an ion of interest is introduced into an ion trap held at low temperature which has a valve or other means to introduce a pulse of complexing gas into the ion trap, wherein the complexing gas is selected from the group consisting of hydrogen (in a hydrogen/helium mixture, preferably at 20:80 V:V), hydrogen ($H_2$), helium (He), argon (Ar), neon (Ne), krypton (Kr), xenon (Xe), carbon dioxide ($CO_2$), carbon monoxide (CO), nitrogen ($N_2$), methane ($CH_4$), and sulfur hexafluoride ($SF_6$). The complexing gas is pulsed into the ion trap containing the ion of interest for a period sufficient to produce gas-ion adducts as otherwise described herein. It is noted that in the present invention, the pulsing of the complexing gas into the ion trap (note that it is highly preferred that the gas can be pulsed into the low temperature trap followed by the introduction of ions to produce gas-ion adducts or alternatively, in certain instances, it may be possible for ions residing within the trap to be exposed to the pulsed gas to produce the gas-ion adducts) and the subsequent extraction delay efficiently produces gas-ion adducts which can be analyzed further using mass spectrometry (time of flight, quadrupole, ion cyclotron resonance, etc) to confirm the molecular mass of the gas-ion adducts, separated and further subjected to infrared spectroscopy (vibrational predissocation spectroscopy) to provide high resolution determination of the functional groups in the ion of interest. Pursuant to the present invention, the resolution of the infrared spectrum which is produced using gas-ion adducts according to the present invention are substantially more highly resolved spectral signatures than spectra which can be produced by analyzing the naked ion of interest. It is noted that in the present invention, the use of UV and/or visible spectroscopy, alone or in combination with vibrational spectroscopy (IR) and mass spectrometry may be used to more fully identify and/or characterize an ion of interest.

In a first aspect, the present invention relates to a method for producing gas-ion adducts in a low temperature controlled ion trap of a mass spectrometry apparatus comprising exposing resident ions of interest in said ion trap at low temperature to a complexing gas or gas mixture which is pulsed into said ion trap, and allowing said ions of interest and said pulsed gas or gas mixture to form gas-ion adducts which are subjected to mass spectrometry analysis and optionally, at least one analysis selected from infrared (vibrational) spectroscopy, uv or ultraviolet (electronic) analysis and visible (vibrational overtone or electronic) spectrum analysis, wherein said complexing gas or gas mixture is selected from the group consisting of a mixture of hydrogen and helium, helium (He), argon (Ar), neon (Ne), krypton (Kr), xenon (Xe), carbon dioxide ($CO_2$), carbon monoxide (CO), nitrogen ($N_2$), methane ($CH_4$), and sulfur hexafluoride ($SF_6$).

In the present invention, the resulting gas-ion adducts, preferably hydrogen-ion adducts or complexes, when extracted and isolated by mass spectroscopy (preferably a time of flight mass spectrometer, although quadrupole and ion cyclotron mass spectrometry may also be used) and subjected to infrared interrogation (preferably using a tunable laser at wavelengths ranging from about 600-4300 $cm^{-1}$), although other infrared spectroscopy methods including fourier transform infrared (FT-IR) as well as dispersive infrared spectroscopy, etc.) can be used to generate infrared spectra of significantly higher resolution than when a non-adduct ion, rather than a gas-ion adduct of the present invention, is analyzed. It is noted here that ultraviolet spectroscopy (UV) and visible spectroscopic methods may be used pursuant to the present methods.

The present invention provides enhanced spectral resolution, especially for complex species such as biomolecules and polypeptides, and can be used in numerous applications for identifying and/or characterizing the interaction of complex biomolecules with small molecules or other biomolecules. These applications include, for example, identifying the structure of complex biomolecules, to monitor the interaction of a complex biomolecule, including a biopolymer such as a complex carbohydrate or polypeptide, including a receptor with a smaller molecule such as a cofactor, modulator or drug molecule, to identify and/or characterize catalytic reactions by enzymes on substrates, to identify and/or characterize interactions of antibodies with immunogens to identify epitopic regions, to identify and/or characterize chemical reactions (including functional group chemistry), to identify and/or characterize the interaction of antibiotics with complex targets such as receptors and/or other proteins, including to learn how proteins and other antibiotic targets have been modified to obtain or achieve drug resistance, among numerous others.

Pursuant to the present invention, it had been unexpectedly discovered that the use of a pulsed cryogenic complexing gas in a low temperature ion trap which contains ions of interest can be used to produce gas-ion adducts as otherwise described herein to provide consistency of high resolution in infrared spectroscopic methods, preferably coupled with mass spectrometry, which result in obtaining high resolution spectra generated for the gas-ion adducts. The method of the present invention may be used and applied in a simple manner to produce exceptional results which are unavailable when more conventional approaches, such as where naked ions (i.e., ions which are not complexed with a complexing gas as otherwise described herein) are used to generate infrared spectra.

In the present invention, a complexing gas selected from the group consisting of hydrogen, helium, argon, neon, krypton, xenon, carbon dioxide or carbon monoxide, preferably a hydrogen/helium mixtures (generally, hydrogen at approximately 5%-50% by volume of a gas mixture comprising hydrogen and an inert gas, preferably helium) at cryogenic temperatures of approximately no greater than about 50 Kelvins (in the case of hydrogen/helium mixtures about 10-20 Kelvins or lower, no higher than about 20 Kelvins, 15 Kelvins, preferably about 10 Kelvins or lower, about 10 Kelvins, 5 Kelvins are used). Using key elements of a mass spectrometer including an ion trap and means to pulse gas into the trap which is kept at very cold temperatures, gas-ion adducts are formed and are analyzed using infrared lasers to produce infrared spectra that may be readily interpreted by chemists and can be directly compared to widely available theoretical calculations of spectra or to reference spectra to identify functional groups on molecules and/or the impact on functional groups in molecules. Spectral resolution obtained using the methods according to the present invention make it feasible to provide interactional (i.e., chemical, etc.) analysis of complex biomolecules, especially including biopolymers and especially carbohydrates and proteins, especially including with small molecules such as drugs.

In the present invention, the inventors have established the use of complexing gas (e.g., preferably $H_2$) "ice" (cryogenic $H_2$ in a mixture of about 10-20% by volume hydrogen in a mixture of hydrogen and an inert gas such as helium or other inert gas) attached to large ions at low temperature in quadrupole ion traps as a means to obtain very sharp infrared spectra of complicated objects that do not yield much information from room temperature infrared (IR) diagnostics available in traditional chemical analysis. By eliminating the condensed phase medium of traditional prior art approaches and creating a very cold, gas phase, preferably $H_2$ solvated ions (gas-ion adducts) which are exposed to infrared radiation within the range of about 600-4300 $cm^{-1}$, these reveal intrinsically sharp vibrational (infrared) spectral signatures arising from individual functional groups, thus providing a means by which the chemical structure of chemical compounds and in particular, large chemical compounds such as biopolymers, including complex carbohydrates and proteins and other polypeptides including target sites of drugs and/or antibodies may be analyzed much more accurately than using prior art methods.

In a preferred method according to the present invention, as set forth in attached FIG. 1, ion formation (1) provides ions which are to be analyzed. Any means by which an ion in a gas phase is provided may be used. Once the ions are created, they are preferably injected into a vacuum tube (2) and passed along the tube which contains a number of regions which exposes/propagates the ions to progressively stronger vacuum (e.g., in FIG. 2, reduced pressure from 1.5 torr down to $3 \times 10^{-7}$ torr) (3), (4) (5) and (6). At the end of the vacuum tube, a means to remove non-ionic material is provided and in FIG. 1 this element is referred to as an ion bender (7). In the ion bender (7), the ions are exposed to an electromagnetic or other field which guides ions of interest into the ion trap (8) to the exclusion of non-ions. Once in the ion trap which is kept at very low temperatures, the resident ions are exposed to a complexing gas selected from the group consisting of $H_2$ (in a $H_2$/helium gas mixture), hydrogen ($H_2$), helium (He), argon (Ar), neon (Ne), krypton (Kr), xenon (Xe), carbon dioxide ($CO_2$), carbon monoxide (CO), nitrogen ($N_2$), methane ($CH_4$) or sulfur hexafluoride ($SF_6$) for a period (from 1 to about 100 millisecond, about 50-95 milliseconds, about 70-90 milliseconds) sufficient to produce gas-ion adducts which can be further analyzed. Once the gas-ion adducts are produced, they are then exposed to an extraction region (9), preferably a Wiley-McLaren mass spectrometer which separates gas-ion adducts from ions which have not been complexed with gas (naked ions). (mass spectrometer is used to separate out and identify specific gas-ion adducts for analysis, where applicable) followed by infrared spectrometer (labeled ion optics 10) where analyses to determine the mass of the adducts (mass spectrometry will provide data which evidences the number and type of gas-ion adducts which have been produced) as well as the functional groups on the ion of interest.

Figure 2:
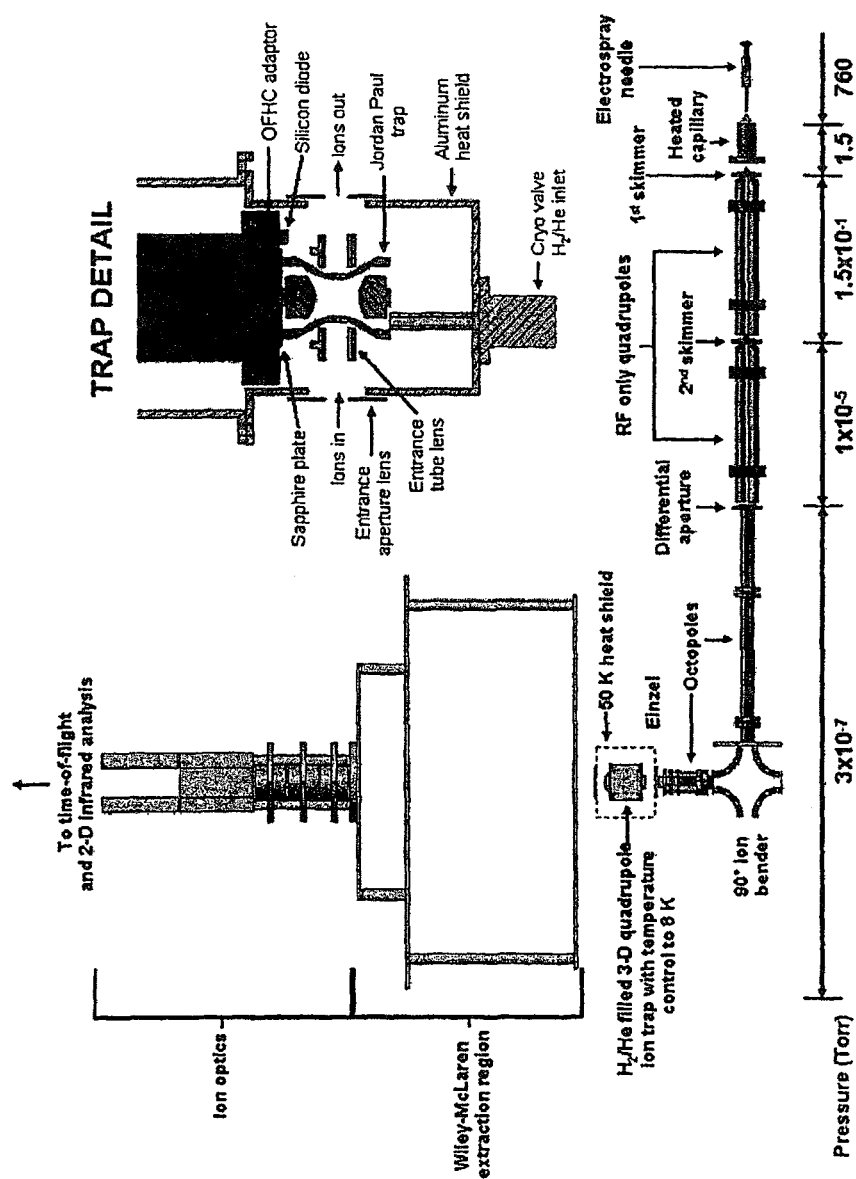
FIG. 2 shows a schematic diagram (to scale) of the ESI ion source interfaced to the cold RF ion trap and time-of-flight (TOF) mass spectrometer. The ESI-generated ions are guided through two differentially pumped stages by two RF only quadrupoles to a differential aperture leading into the final vacuum envelope. Octopole ion guides and a 90° turning quadrupole deflector direct the beam to a series of focusing elements before injection into the cryogenically cooled Paul trap, where ions are collisionally cooled and tagged with $H_2$ (see Trap Detail). Upon ejection from the trap, ions are allowed to drift into the main extraction region before coaxial acceleration focuses them at the laser interaction region of the tandem TOF photofragmentation spectrometer.

A preferred system for performing the present invention is set forth in detail in attached FIG. 2. In this aspect of the invention, the mass spectrometer apparatus used to conduct the present invention utilizes the widely used and versatile electrospray ionization (ESI), coupled to a low temperature (about 10K) Jordan Paul ion trap, through a vacuum tube containing four regions of increasing vacuum on the ions which flow through the vacuum tube. In the ion trap, $H_2$ molecules are condensed on the target ion using a pulsed mixture of $H_2$ and helium (preferably at a ratio of 20:80 V:V). The improved performance of the present invention occurs by pulsing the $H_2$/He gas mixture at 20:80 V:V into the ion trap. This pulsing of the gas enables $H_2$ (and other gasses) to form complexes/adducts with ions of interest at low temperature. The method of the present invention is highly reliable and produces adducts with ions in numerous circumstances. This was not the case in prior art methods which did not utilize the present invention, and which suffered from significant inconsistencies and unreliability which was not generalizable to a large number of chemical compounds to be analyzed, regardless of the functional group chemistry to be analyzed. In the present invention, after the formation of the gas-ion adducts, these are then introduced into a mass spectrometer (e.g., a triple-focusing photofragmentation mass spectrometer) utilizing time of flight techniques followed by infrared spectrometry, where vibrational spectra of the mass-selected ions are obtained using pulsed infrared lasers (preferably, widely used "table-top" tunable pulsed infrared lasers between 600 and 4300 $cm^{-1}$). Isomer-selective spectra may also be used, where two such lasers are employed in a hole-burning scheme. Large biomolecules, including carbohydrates and peptides yield surprisingly clean and interpretable infrared spectra with this approach. The applications of the present invention to the pharmaceutical sciences, biochemistry and related sciences represents a significant advance in the arts.

Thus, in one aspect of the present invention (see FIG. 2), ions which have been introduced into an ion trap of a mass spectrometer are exposed to a pulsed gas mixture of hydrogen and an inert gas, preferably a $H_2$/He mixture of about 20:80 V:V in the ion trap, in order to form hydrogen/ion adducts; and the hydrogen/ion adducts are then extracted (to remove non-adduct or "naked" ions), exposed to mass spectrometric time of flight analytical techniques and one or more pulsed infrared lasers; and vibrational spectra are obtained for the laser exposed gas-ion adducts. Further optional and preferred steps according to the present method include providing a sample by dissolving a compound into an appropriate solvent; generating electrospray ions from said solution, propagating the electrospray produced ions in the presence of reduced pressure (preferably using radio-frequency ion guides) over a series of progressively reduced pressure regions along a vacuum tube(s) exposed to quadrupoles and/or octopoles (or any type of ion guides) in order to provide a high percentage of ions in gas form, optionally turning the ions 90 degrees (or otherwise exposing the ions to an electromagnetic field(s) to separate/purify them from non-ions) before passing the propagated ions into an ion trap, exposing the ions in the ion trap to a pulsed complexing gas (e.g. hydrogen in a hydrogen helium mixture), wherein the pulse of gas ranges from less than 1 millisecond (about 500 microseconds) to about 100 milliseconds, about 1 millisecond to about 50 milliseconds, about 1 millisecond to about 10 milliseconds, preferably about a 1 millisecond pulse) of a hydrogen/inert gas mixture at temperatures ranging from very low to room temperature or above, preferably about room temperature. The introduction of complexing gas into the ion trap at a temperature substantially above the ion trap temperature is provided so that as the gas which is pulsed into the ion trap is cooled at low temperature, maximum interaction with resident ions takes place to form gas-ion adducts. The ion trap is kept at a low temperature, generally below about 50 degrees Kelvin (depending upon the complexing gas used), preferably no greater than about 30-40 degrees Kelvin (in the case of hydrogen complexing gas, no greater than about 15-20 degrees Kelvin, preferably no greater than about 10 degrees Kelvin, or about 5-10 degrees Kelvin) to produce gas-ion adducts, preferably H$_2$-ion adducts.

Once the gas-ion adducts are formed, these gas-ion adducts are extracted from naked ions (i.e., non-adduct ions), preferably in an extraction stack (e.g. a Wiley-McLaren extraction stack) (FIG. 2), and the concentrated gas-ion adducts are subsequently exposed to mass spectrometry to determine the molecular weight of the gas-ion adducts which are analyzed by infrared (predissociation vibrational) spectrometry (and optionally, visible and/or UV spectroscopy). In the infrared analysis, the extracted adducts are exposed to at least one laser beam (tunable) between 600 and 4300 cm$^{-1}$.

In a preferred aspect, the present invention (see FIG. 2) relates to a method for generating high resolution infrared (photon energy cm$^{-1}$) spectra of mass-selected ions comprising the steps of:

2. Providing a solution (or solid/gas mixture) of a compound (sample) to be analyzed;
3. Providing (e.g., electrospray, pulse valve/electron gun, electric impact, chemical ionization, laser ablation, free jet) ions from said solution (or solid/gas mixture);
4. Passing (by injection, other means) the ions from step 2 into a vacuum tube (e.g. RF guide) comprising multiple (i.e., at least two, or alternatively three, four or more) regions of progressively increasing vacuum (differentially pumped regions of lowered pressure) and propagating the ions through the regions;
5. At the distil end of the vacuum tube in step 3, optionally turning said ion stream 90° (e.g. using a DC quadrupole) to remove non-ions before introducing the propagated ions into a low temperature ion trap cooled to no greater than about 50 Kelvins (no greater than about 30 Kelvins, no greater than about 20 Kelvins, preferably no greater than about 10 Kelvins);
6. Introducing a pulsed complexing gas (preferably a mixture of hydrogen and helium 20:80 V:V, but alternatively a gas selected from the group consisting of helium, argon, neon, krypton, xenon, nitrogen, methane, carbon dioxide or carbon monoxide) mixture at a temperature ranging from about 10 degrees Kelvin up to room temperature (preferably at about room temperature to allow the gas to condense in the presence of ions in the ion trap which are kept at very low temperature) into said ion trap and storing the ions and the complexing gas in the ion trap for a period sufficient to form a mixture of gas-ion adducts comprising a complex of gas (preferably, H$_2$) and said ions of interest and non-adduct (naked) ions;
7. Extracting the gas-ion adducts and naked ions form the ion trap, preferably into a Wiley-McLaren mass spectrometer which performs the extraction;
8. Exposing said adducts to mass spectrometry (preferably, time of flight, but also as otherwise described herein) and infrared light source to generate a fragment ion density (and optionally, U/V and/or visible spectroscopy); and
9. Obtaining vibrational spectra (and/or UV, visible spectra) for the exposed (preferably laser exposed) ions.

As discussed, the general method according to the present invention is exemplified by the schematic which is presented in general form in attached FIG. 1. A more preferred method is exemplified by the apparatus which is set forth in FIG. 2, hereof.

DETAILED DESCRIPTION OF THE INVENTION

The following terms are used to describe the present invention. In instances where a term is not described, the term is used within context, as those of ordinary skill would use.

The term "sample" shall mean any compound, in any state, within context, which is to be ionized or which has been ionized. In many instances, the term sample shall be used to describe a compound or ion in solution or in a gas step which is to be subject to analysis used methods described herein.

The term "ion" shall be used to describe a charged molecule which is produced or obtained from a sample compound. The ion may be negatively charged, positively charged, zwitterionic or multiply charged (negative, positive or zwitterionic), especially where the compound is a biopolymer, especially including a complex carbohydrate or polypeptide. An "ion of interest" is a particular ion which is to be analyzed using the methods according to the present invention. In most instances an "ion" and an "ion of interest" are both directed to the same charged chemical species. The term "naked ion" or "non-adduct" ion refers to an ion of interest which is not complexed with a gas in adduct form.

The term "gas-ion adduct" is used to describe an ion which is complexed with a complexing gas in the ion traps of mass spectrometers and analyzed according to the present invention. The adduct may be a complex of one or more hydrogen or other gas atoms and an ion. It is the gas-ion adduct upon which laser spectrometery is used to provide highly resolved infrared spectra (photon energy cm$^{-1}$) of functional groups (as otherwise described hereinbelow). Pursuant to the present invention, the mass spectrometer provides spectral evidence of the molecular weight (in particular, the number of gas molecules which are complexed with the ion of interest) of the gas-ion adduct to which is subsequently subjected to laser spectroscopy pursuant to the present invention.

The term "gas" or "complexing gas" is used to describe a gas selected from the group consisting of hydrogen (preferably presented as a hydrogen/helium mixture), helium (He), argon (Ar), neon (Ne), krypton (Kr), xenon (Xe), carbon dioxide (CO$_2$), carbon monoxide (CO), nitrogen (N$_2$), methane (CH$_4$), and sulfur hexafluoride (SF$_6$) which complexes with an ion of interest to form a gas-ion adduct in an ion trap as otherwise described herein at low temperature. Hydrogen-ion adducts which are produced according to the present method are preferred.

The term "vacuum tube" is used to describe a tube in which ions are subjected to low pressure in order to propagate the ions before entering an ion trap as otherwise described herein. In preferred aspects as presented in FIGS. 1 (2) and 2, the vacuum tube is preferably segmented into at least two regions and preferably at least 3-4 regions which apply an increasing vacuum on the ions which pass through the different regions in order to provide the ions in a gaseous state as the ions are introduced into the ion trap.

The term "electrospray" refers to a preferred method for providing ions according to the present invention. In the present invention, ions of interest may be prepared by numerous methods available in the art, including, for example, electrospray, pulse valve/electron gun, electric impact, chemical ionization, laser ablation, etc. Electrospray is a system which is created preferably in an electrospray syringe which is exposed to an electromagnetic field. In electrospray ion formation, a liquid containing the analyte(s) of interest is dispersed by electrospray into a fine droplet aerosol. Because the ion formation involves extensive solvent evaporation, the typical solvents for electrospray ionization are prepared by mixing water with volatile organic compounds (e.g. methanol, acetonitrile, etc.). To decrease the initial droplet size, compounds that increase the conductivity (e.g. acetic acid, formic acid, other organic acids) are often added to the solution. Large-flow electrosprays can benefit from additional nebulization by an inert gas such as nitrogen. The solvent evaporates from a charged droplet until it emits charged ions which are used for analysis.

The term "ion concentrator" or "ion bender" is used to describe an optional part of a mass spectrometer used in the present invention which applies an electric field to a sample of the ions which are introduced into the ion trap in order to separate/purify ions from non-ions (neutral species) which are to be introduced into the ion trap. Ion concentrators according to the present invention may be of a variety of types, but a preferred concentrator is an ion bender which bends the ions in a sample to separate ions (which respond to an electrical field) from non-ionic particles, in an effort to have a purified sample enter the ion trap, wherein gas-ion adducts will be formed from the ions and a complexing gas.

The term "ion trap" is used to describe an electrical and/or magnetic field that captures ions in a region of a vacuum system, in the present invention, within the mass spectrometer. Ion traps are used in the present invention in mass spectrometry for trapping ions. The most common types of ion traps are the Penning trap, the Paul trap (quadrupole ion trap) and the multipole trap. A preferred ion trap for use in the present invention is the Jordan Paul trap, which is set forth in FIGS. 2 and 2A.

An ion trap mass spectrometer may incorporate a Penning trap (Fourier transform ion cyclotron resonance), a Paul (Jordan Paul) trap (8 in FIG. 1, in FIG. 2 or 2A, or as otherwise described herein) or a Kingdon trap. The Orbitrap, which also may be used, was introduced a number of gears ago and is based on the Kingdon trap. Other types of mass spectrometers may also use a linear quadrupole ion trap as a selective mass filter. In aspects of the invention, the ion trap has both a gas inlet (8A) to allow gas into the ion trap, as well as a pulse valve (8B) which pulses the gas preferably at room temperature into the ion trap which is kept at very cold temperatures, at intervals ranging from less than about 1 millisecond to about 100 milliseconds, preferably about 50-100 ms, about 65-95 ms, about 70-90 ms. It has been unexpectedly discovered that the pulsing of a complexing gas in an ion chamber at very low temperature in the presence of ions will efficiently produce gas-ion adducts which provide high resolution when analyzed using infrared spectroscopy.

The term "pulse" or "pulsing" refers to the introduction of complexing gas or gas mixture into the ion trap containing ions of interest which are to be complexed with the complexing gas to form gas-ion adducts, which are further analyzed using mass spectrometry, infrared spectroscopy and optionally ultraviolet and visual spectroscopy. The main point about pulsing is that it is highly preferred to have the gas in the trap when the ions enter it to slow them down so that they do in fact trap and form adducts. The gas cools in the cold metal enclosure with the ions until the complexing gas (e.g. $H_2$) begins to condense on the trapped ions. This takes tens of milliseconds in the preferred Jordan trap. Because the gas is shut off in a few milliseconds or less (pulsed), the gas is being pumped out through the holes in the trap (which may be the same ones that let the ions in), and there is a need to wait until the pressure falls low enough (by about a factor of 50-100 from the peak) so that the ions can be removed with extraction voltages (typically tens of volts on the plates) without having them collisionally warmed up, thus losing the gas from the gas-ion adducts on the way out. So it is pulse in (gas), trap (ions), cool, condense, evacuate, extract.as a preferred sequence, but it is possible that the pulse and trap steps may be reversed so long as the gas and ions are condensed within the ion trap to form gas-ion adducts. The introduction of the gas into the trap is achieved through a tube that connects an outside reservoir to the trap. The tube is closed by a solenoid valve which opens for about 1 ms and lets a short burst of gas into the trap. This is in contrast to prior art in which the gas is continuously leaked into the trap.

The term "mass spectrometer" is used to describe an apparatus which is used in the present invention to describe a principal method according to the present invention that measures the mass-to-charge ratio of charged particles and provides evidence of the existence of gas-ion adducts which are being analyzed by infrared spectroscopy hereunder. Mass spectrometers are generally used for determining masses of particles, for determining the elemental composition of a sample or molecule, and for elucidating the chemical structures of molecules, such as peptides and other chemical compounds. The principle of mass spectrometry consists of ionizing chemical compounds to generate charged molecules or molecule fragments and measuring their mass-to-charge ratios. In a typical mass spectrometric procedure a sample is loaded onto the mass spectrometer, and the sample undergoes vaporization. Thereafter, the components of the sample are ionized by one of a variety of methods (e.g., by electrospray methods, by impacting them with an electron beam, by laser ionization or laser desorption, etc. as otherwise described herein) which results in the formation of charged particles (ions). The ions are separated according to their mass-to-charge ratio in an analyzer by electromagnetic fields. The ions are detected, usually by a quantitative method and the ion signal is processed into mass spectra. In most applications, mass spectrometers consist of three modules including an ion source, which can convert gas phase sample molecules into ions (or, in the case of electrospray ionization, move ions that exist in solution into the gas phase), a mass analyzer, which sorts the ions by their masses by applying electromagnetic fields and a detector, which measures the value of an indicator quantity and thus provides data for calculating the abundances of each ion present.

Mass spectrometry has both qualitative and quantitative uses. These include identifying unknown compounds, determining the isotopic composition of elements in a molecule, and determining the structure of a compound by observing its fragmentation. Other uses include quantifying the amount of a compound in a sample or studying the fundamentals of gas phase ion chemistry (the chemistry of ions and neutrals in a vacuum).

In certain aspects of the invention, electrospray ionization is used, especially when ionizing samples of large biomolecules. The term "electrospray ionization" or "ESI" is a preferred technique used in the present invention in mass spectrometry to produce ions, especially ions of macromolecules, especially including biopolymers. It is especially useful in producing ions from macromolecules because it overcomes the propensity of these molecules to fragment when ionized. Mass spectrometry using ESI is called electrospray ionization mass spectrometry (ESI-MS) or, less commonly, electrospray mass spectrometry (ES-MS), a preferred method of mass spectrometry which is combined with infrared spectroscopy in the present invention.

The term "time-of-flight mass spectrometry", "time-of-flight" and "TOFMS" are used synonymously to describe a particular (and preferred for use in the present invention) method of mass spectrometry wherein an ion's mass-to-charge ratio is determined via a time measurement. In time-of-flight mass spectrometry, ions are accelerated by an electric field of known strength. The acceleration results in an ion having the same kinetic energy as any other ion. The velocity of the ion depends on the mass-to-charge ratio. The time that it subsequently takes for the particle to reach a detector at a known distance is measured. This time will depend on the mass-to-charge ratio of the particle (heavier particles reach lower speeds). From this time and the known experimental parameters one can find the mass-to-charge ratio of the ion. Using this method, the various gas-ion adducts may be identified readily, in conjunction with infrared spectrometric analyis of the same adducts. Other time-based methods that sort ions of the same kinetic energy, such as reflectron time of flight, are also used in "time of flight mass spectrometry".

The term "infrared spectroscopy" or "IR spectroscopy" is directed to a chemical analysis which deals with the infrared region of the electromagnetic spectrum, in particular a wavelength ranging from, about 600-4300 $cm^{-1}$, which is used to study fundamental vibrations and associated rotational-vibrational structures. It covers a range of techniques, mostly based on absorption spectroscopy. As with all spectroscopic techniques, it can be used to identify and study chemicals. A common laboratory instrument that uses this technique is a Fourier transform infrared (FTIR) spectrometer. Dispersive spectrometers are also quite common and may be used in the present invention. A preferred infrared system used to practice the present invention is a system based on an optical parametric oscillator (OPO) followed by an optical parametric amplifier (OPA) commercially available from Laser Vision, Bellevue Wash., USA (deanguyer.com). The basic outline of what happens is that moderate energy photons at a particular wavelength (1064 nm) enter the OPO/OPA crystal chain. These photons are generated by a commercially available YAG laser. As each of these photons enters the crystal chain, nonlinear optical effects split them into two photons that sum to the energy of the original photon in a predictable and well defined manner. One of these new photons happens to be in the 600-4300 $cm^{-1}$ range. By adjusting the angle of the crystals relative to the incident light, we can tune the light across the entire 600-4300 $cm^{-1}$ range. In addition to the OPO/OPA laser system, alternative systems include, for example, the Quantum Cascade Laser (QCL) and the Diode Laser, both well-known in the art. Other infrared lasers may also be used, including free-electron lasers based on generation of light by manipulating very high energy electrons through electric and magnetic fields.

The term "functional group" shall mean any functional group of a chemical compound having a bond within an adduct which is identified with a particular wavelength ($cm^{-1}$) and can be measured by an infrared spectrometer. Representative, common functional groups include include the following.

C—O 1000-1300 $cm^{-1}$ Alcohols and esters
N—H 1580-1650 $cm^{-1}$ Amine or amide
C=C 1610-1680 $cm^{-1}$ Alkenes
C=O 1650-1760 $cm^{-1}$ Aldehydes, ketones, acids, esters, amides
O—H 2500-3300 $cm^{-1}$ Carboxylic acids (very broad band)
C—H 2850-3000 $cm^{-1}$ Alkane
C—H 3050-3150 $cm^{-1}$ Alkene (Compare intensity to alkane for rough idea of relative number of H atoms involved.)
O—H 3230-3550 $cm^{-1}$ H-bonded in alcohols
N—H 3300-3500 $cm^{-1}$ Amine or amide
O—H 3580-3670 $cm^{-1}$ Free —OH in alcohols (only in samples diluted with non-polar solvent)
C≡C 2100-2300 $cm^{-1}$ Triple carbon-carbon bond in alkyne
C≡N 2100-2300 $cm^{-1}$ Triple carbon-nitrogen bond in cyano
$CO_2$ 2380 $cm^{-1}$ Carbon dioxide The term "extraction region" or "extraction field region" is used to describe an area in a mass spectrometer through which ions pass after forming gas-ion adducts in the ion trap in order to extract out naked ions from gas-ion adducts which are subsequently analyzed by mass spectrometry and infrared spectroscopy. The extraction region applies an electromagnetic field to the ions which are passed through and in doing so can extract out naked ions from according to the present invention. In the present invention, a Wiley-McLaren extraction region is used to purify gas-ion adducts from naked ions through mass spectrometry and prior to infrared spectroscopy analysis.

As discussed above, preferred methods according to the present invention make use of the systems which are presented in FIGS. 1 and 2 hereof. In a preferred method according to the present invention, a general apparatus according to the present invention, as set forth in attached FIG. 1, ion formation (1) provides ions to be analyzed in the present method. In short, any means by which an ion in a gas phase is provided from a sample in solvent may be used. Ion formation is preferably provided using an electrospray needle as set forth in attached FIG. 2, but alternative approaches for ionizing compounds of interest to produce ions of interest are available in the art, including for example ionization using a pulse valve with an electron gun, photoionizing the sample, creating ions in a sample using electric impact, chemical ionization, laser ablation, etc. Once the ions are created, they are preferably injected into a vacuum tube (2) and passed along the tube which contains a number of regions which exposes the ions to progressively stronger vacuum (e.g., in FIG. 2, reduced pressure from 1.5 torr down to $3 \times 10^{-7}$ torr) (3), (4) (5) and (6). In the preferred apparatus of FIG. 2, four progressively reduced pressure regions are provided as indicated. At the end of the vacuum tube, a means to remove non-ionic material is provided (FIG. 1), and in FIG. 1, this is referred to as an ion bender (7). In the ion bender (7), the ions are exposed to an electromagnetic or other field which guides ions of interest into the ion trap (8) to the exclusion of non-ions, which pass along with bender into an area away from the ion trap. Once in the ion trap which is kept at very low temperatures within the range of about 5 to about 50 Kelvins (depending on the gas used to form complexes with the ions), the resident ions are exposed to a complexing gas selected from the group consisting of $H_2$ (in a $H_2$/helium gas mixture), helium (He), argon (Ar), neon (Ne), krypton (Kr), xenon (Xe), carbon dioxide ($CO_2$), carbon monoxide (CO), nitrogen ($N_2$), methane ($CH_4$), and sulfur hexafluoride ($SF_6$) for a period (from 1 to about 100 millisecond, about 50-95 milliseconds, about 70-90 milliseconds) sufficient to produce gas-ion adducts which can be further analyzed. The gas is pulsed into the ion chamber in order to maximize the formation of gas-ion adducts. Detailed diagrams of ion traps used in the present invention are presented in FIGS. 2, 2A and 2B hereof. Once the gas-ion adducts are produced, they are brought to an extraction region (9), preferably a Wiley-McLaren extraction region which separates gas-ion adducts from ions which are not complexed with gas (naked ions or non-adduct). The gas-ion adducts which have been extract from the naked ions are then passed into the mass spectrometer and infrared spectrometer (labeled ion optics 10) where analyses to determine the mass of the adducts (mass spectrometry will provide data which evidences the number and type of gas-ion adducts which have been produced) from the mass spectrometry analysis as well as the functional groups on the ion of interest by virtue of the infrared analyses. It is noted that each of the gas-ion adducts which are produced will provide exceptional resolution in the infrared (as well as UV and visible) analysis and the fact that there are a different number of gas molecules which are complexed to the ion of interest will have little impact on the resolution of the infrared spectra (vibrational predissociation spectra) which are produced.

A preferred system for performing the present invention is set forth in detail in attached FIG. 2. In this aspect, the mass spectrometer apparatus used to conduct the present invention utilizes the widely used and versatile electrospray ionization (ESI), coupled to a low temperature (about 10K) Jordan Paul (see FIGS. 2A and 2B for additional detail-alternatively, a radio frequency or RF quadrupole ion trap may also be used, among other ion traps). The ion trap is coupled to the ionization chamber through a vacuum tube containing four regions for providing increasing vacuum (reduced pressure) on the ions which flow through the vacuum tube. The ions in gas form are propagated in the vacuum tube. In the ion trap, $H_2$ molecules (preferably at room temperature, although any temperature which allows the gas to condense in the ion traps and condense with the ions resident in the ion trap is applicable) are condensed on the target ion using a pulsed mixture of $H_2$ and helium (preferably at a ratio of about 20:80 V:V). The improved performance of the present invention occurs by pulsing the gas mixture (in this case, a $H_2$/He gas mixture at 20:80 V:V, although a number of other complexes gasses may be used with modification to the temperature at which the ion trap is kept and the pulse rate of the gas intake) in the ion trap. This pulsing of the gas enables $H_2$ (and other gasses) to form complexes/adducts with ions of interest at low temperature. The method of the present invention is highly reliable and produces adducts with ions in numerous circumstances. This was not the case in prior art methods which did not utilize the present invention, and which suffered from significant inconsistencies and unreliability which was not generalizable to a large number of chemical compounds to be analyzed, regardless of functional group chemistry. In the present invention, after the formation of the adducts, these are then introduced into a mass spectrometer (e.g., a triple-focusing photofragmentation mass spectrometer) followed by infrared spectrometry, where vibrational spectra of the mass-selected ions are obtained using pulsed infrared lasers (preferably, widely used "table-top" tunable pulsed infrared lasers between 600 and 4300 $cm^{-1}$). Isomer-selective spectra may also be used, where two such lasers are employed in a hole-burning scheme. Numerous chemicals, including a variety of drugs, organic chemicals, macromolecules and large biomolecules, including carbohydrates and peptides (including antibodies) yield surprisingly clean and interpretable infrared spectra with this approach.

Thus, in one aspect of the present invention (see FIG. 2), ions which have been introduced into an ion trap of a mass spectrometer are exposed to a pulsed gas mixture of hydrogen and an inert gas, preferably a $H_2$/He mixture of about 20:80 V:V in the ion trap, in order to form hydrogen/ion adducts; and the hydrogen/ion adducts are then extracted (to remove non-adduct or "naked" ions, exposed to one or more pulsed infrared lasers; and vibrational spectra are obtained for the laser exposed gas-ion adducts. Further optional and preferred steps according to the present method include providing a sample by dissolving a compound into an appropriate solvent; generating electrospray ions from said solution (using, for example, an electrospray needle, among other approaches), propagating the electrospray ions in the presence of reduced pressure (preferably using radio-frequency ion guides) over a series of progressively reduced pressure regions along a vacuum tube(s) exposed to quadrupoles and/ or octopoles in order to provide a high percentage of ions in gas form, optionally exposing the ions at the distill end of the vacuum tube to a field to separate/purify them from non-ions (e.g., by turning the ions 90 degrees) before passing the propagated ions into the ion trap, exposing the ions in the ion trap to a pulsed complexing gas (e.g. hydrogen in a hydrogen helium mixture, helium, argon, neon, krypton, xenon, carbon dioxide, carbon monoxide, nitrogen, methane, and sulfur hexafluoride, wherein the pulse of gas ranges from less than 1 millisecond (about 500 microseconds) to about 100 milliseconds, about 1 millisecond to about 50 milliseconds, about 1 millisecond to about 10 milliseconds, preferably about a 1 millisecond pulse) wherein the complexing gas is introduced into the trap at temperatures ranging from very low to room temperature or above, preferably room temperature, so that as the gas is cooled it is condensed in the ion trap at low temperature, maximizing interaction with resident ions to form gas-ion adducts. The ion trap is kept at a low temperature, generally below about 50 degrees Kelvin (depending upon the complexing gas used), preferably no greater than about 30-40 degrees Kelvin (in the case of hydrogen complexing gas, no greater than about 15-20 degrees Kelvin, preferably no greater than about 10 degrees Kelvin, or about 5-10 degrees Kelvin) to produce the gas-ion adducts, preferably $H_2$-ion adducts.

Once the gas-ion adducts are formed, these gas-ion adducts are extracted from naked ions (i.e., non-adduct ions), preferably in a Wiley-McLaren extraction stack (FIG. 2), and the concentrated gas-ion adducts are subsequently exposed to mass spectrometry to gauge the molecular weight of the gas-ion adducts which are analyzed by infrared (predissociation vibrational) spectrometry. In the infrared analysis, the extracted adducts are exposed to at least one laser beam (tunable) between 600 and 4300 $cm^{-1}$. In the case of mass spectrometry, time of flight spectra are prepared. In addition, photoelectron time-of-flight (TOF) spectra may be collected and converted to kinetic energy spectra. Electron binding energy spectra may be obtained by subtracting the kinetic energy spectra from the detachment photon energy used.

The present invention may be used in a number of ways which are not intuitive from the prior art, and represent the present invention in its place as recognition in advancing the art.

For example, in the sequencing of biopolymers (proteins and polypeptides) with mass spectrometry, large molecules are broken apart and the weight of the various fragments are analyzed to recover the original sequence. This is a foundation technology for the field of proteomics. The present method using vibrational spectrometry (IR as described herein) can be used to both characterize the shape of the starting material, but more importantly, can be used to structurally characterize the fragments. This is especially useful if the fragments undergo unexpected rearrangements that can complicate recovery of the correct sequence.

It is noted that the main value of gas-ion tagging is that the IR spectra can be obtained at high resolution with very weak laser sources (for example), which is not the case for the alternative, infrared multiplephoton (or multiphoton) dissociation (IRMPD). The present method thus makes it much more commercially viable for infrared sources which have had less significance in the field of use.

In addition to identifying and/or characterizing the functional groups on organic molecules (such term including any organic compound, including a drug and/or cofactor), there is also utility in characterizing the ligand binding in organometallics, especially when these species correspond to unstable reaction intermediates in a catalytic cycle.

Pursuant to the present invention, the bandwidth of the vibrational transitions recovered by the tagging approach is vastly improved many groups and especially for dangling NH (amide A) or OH groups. These are typically 50 cm$^{-1}$ or larger in solution and become 6 cm$^{-1}$ or less in a tagging measurement. This allows access to the behavior of proton donors in H-bonded interaction that are not usually available in solution measurements because the bands are too broad. The other regions of particularly enhanced performance are the amide I and II ranges. The amide I bands arise from the C=O bond stretches and are about 30 cm$^{-1}$ in room temperature solutions. These are typically 6 cm$^{-1}$ when observed with tagging, an improvement that enables local structural characterization of individual C=O oscillators in complex structures.

Further pursuant to the present invention, the bandwidths of the vibrational transitions observed with tagging pursuant to the present invention are also about a factor of 4 narrower than those reported with IRMPD of room temperature bare ions. This substantially enhanced resolution arises because flexible molecules have their transitions spread out as the frequencies of the bonds change as the backbone undergoes thermal fluctuations. These are frozen out in the tagging regime, thus yielding the intrinsically narrow nature of the transitions. IRMPD also yields broader transitions because the method in inherently non linear, and the locations of the various transitions change when each photon is absorbed, and typically tens of photons are required to break covalent bonds.

Analysis of carbohydrates represents an additional aspect of the invention, especially where the large number of isomers available for sugars (especially including isometric sugars of simple sugars such as monosaccharides, disaccharides or oligosaccharides) should yield very different vibrational spectra that will allow a fast and straightforward way to sort out compositions.

The method of the present invention is easily interfaced with several laser sources to carry out isomer-specific spectroscopic characterization using photochemical hole burning. Efficient tagging also opens up a new way to rationally synthesize reaction intermediates by colliding reactive species (e.g., water, carbon dioxide, hydrocarbons) with the tagged (complexed) ion, creating transient species through the rapid evaporation of the tags (hydrogen or other adducts). The products can then be tagged again with the same (or different) complexing gas, thus allowing their characterization with vibrational spectroscopy. This provides a new approach for establishing the pathways for catalytic activation of small molecules.

While the present invention emphasizes vibrational (IR) spectroscopy because it is universal, the tagging method works in the same manner to obtain UV/VIS spectra, thus enabling a full spectral characterization of compounds with the sensitivity of mass spectrometry.

The following examples are provided to further describe the invention. The following descriptions are not to be taken to limit the invention in any manner.

EXAMPLES

Reference Set 1 Applies to the Discussion in these Examples

Experimental Details $H_2$ Tagging in the Quadrupole Trap with Pulsed Buffer Gas A schematic diagram of the recently completed instrument used in this example is displayed in FIG. 2. The time-of-flight (TOF) photofragmentation part of the apparatus, which has been described in detail elsewhere,[35, 36] has been fitted with a new ESI ion source designed closely after the scheme demonstrated by Wang and co-workers.[31] In the present study, anions are produced through electrospray ionization of a ~0.5 mM solution of dodecanedioic acid in an 80/20 solution of methanol and water. The ions are extracted from the electrospray using standard differential pumping techniques, where the first stage (1.5 Torr) involves passing the ions through a heated 0.76 mm diameter capillary (5 cm in length) followed by two more stages (150 mTorr and 10$^{-5}$ Torr, respectively) separated by two 1.5 mm skimmers. After leaving the first skimmer, the ions are guided through the second by custom RF only quadrupoles leading to the final differential aperture (1.5 mm) into the main vacuum envelope, held at a base pressure of 3×10$^{-7}$ Torr. The RF voltage was supplied using the circuit recommended by O'Connor and co-workers. [37, 38] Once inside the main chamber, the beam is guided by an RF octopole to a DC turning quadrupole, which rejects the neutral background, followed by another RF octopole leading to the ion lenses that interface the ion beam to the trap. The key element is the injection of the ESI generated ions into a low temperature (minimum temperature is 8 K) Paul trap (Jordan), where the ions are stored for a carefully controlled time interval prior to being ejected by applying a low voltage pulse (60 V) to one of the trap electrodes. The ejected ions drift into the Wiley-McLaren extraction region of the existing TOF instrument in a coaxial arrangement. Because the ions drift with relatively high kinetic energy into this region, the TOF performance is somewhat degraded, resulting in somewhat broader mass peaks with asymmetrical peak shapes. Once inside, two high voltage pulses accelerate them to a final energy of 3.5 keV, and bring them to a transient focus at the laser interaction region located about 1.5 m from the source.

Figure 2A:
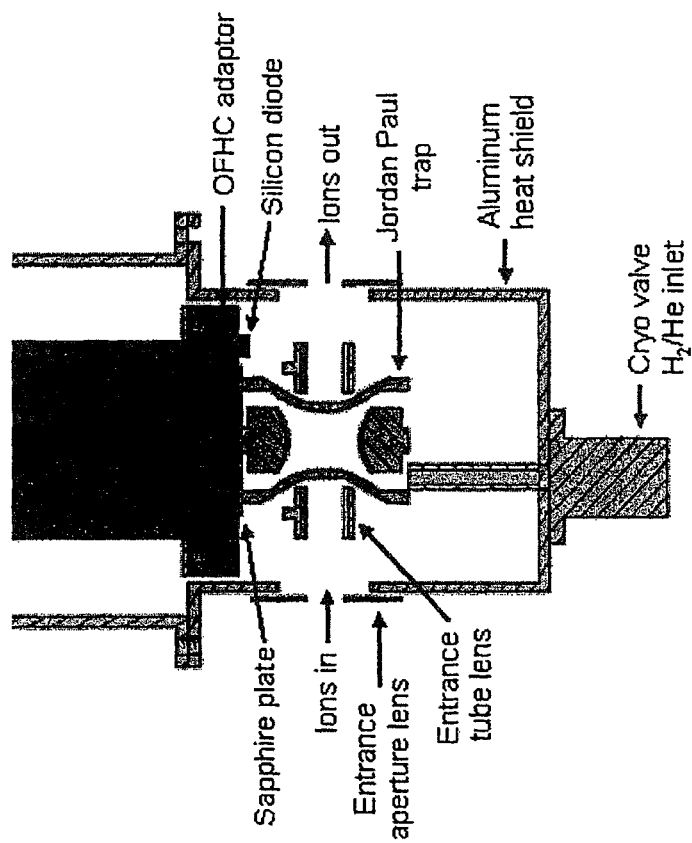
FIG. 2A shows a more detailed presentation of the ion trap which appears in FIG. 2
Figure 2B:
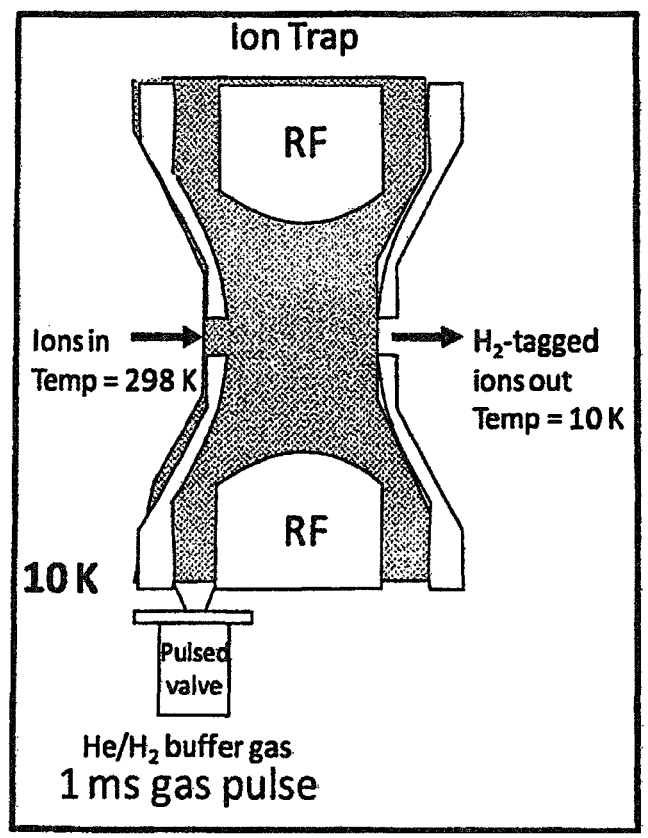
FIG. 2B shows the important features of the ion trap used in the present invention.

The trap is cooled with a closed cycle He cryostat (Sumitomo, 1.5 Watts at 4.2 K) and filled with a burst of gas (20% $H_2$ in He) using a pulsed valve (Parker Series 9) mounted on the 50 K heat shield on the outside of the trap housing (see Trap Detail in FIG. 1). The gas is introduced directly into the trap through a 3.9 mm ID tube that is 3.4 cm long. The trap is mounted to the cold head by an 8.5 mm thick adapter made of oxygen free high purity copper (OFHC) and a 1 mm thick sapphire plate which provides electrical insulation. Indium foil (0.1 mm) is placed between these junctions to maximize thermal conductivity. The silicon diode temperature probe (Lake Shore: D6008610) is placed on the bottom of the OFHC adapter as indicated in FIGS. 2, 2A and 2B (Trap Detail). The valve is pulsed on for 10 ms with a 15 volt square pulse (10 Hz), where the backing pressure is sufficiently low to avoid hydrodynamic flow into the trap. While the exact pressure rise and temperature profile of the buffer gas in the trap are difficult to determine, optimum operation occurs when the He/$H_2$ pulse raises the ambient pressure in the chamber by about 5×10$^{-7}$ Torr. Note that the aperture from the trap to the main chamber is about 3 mm, while the chamber is evacuated with a 2000 L/s diffusion pump (Edwards Diffstak 250).

The performance of the cold Paul trap as a medium for attaching $H_2$ has been documented in the earlier report by Wang and coworkers.[31] That work, however, was carried out with a continuous stream of gas introduced to the trap. It is therefore useful to present the role of the timing sequence in the generation of $^-OOC(CH_2)_{10}COO^- \cdot (H_2)_n$ complexes, which is displayed in the series of mass spectra shown in FIG. 3. The set of sharp peaks toward higher mass are consistent with $H_2$ addition to the $^{12}C_{12}H_{20}O_4^{2-}$ isotopologue, while the small shoulder on the high mass side of the parent peak (denoted by * in trace a) as well as the interlopers in the dominant distribution of higher mass peaks are consistent with the presence of the $^{13}C^{12}C_{11}H_{20}O_4^{2-}$ isotopologue. The latter is calculated to occur with 13.3% of the dominant isotopologue given the 1.1% natural abundance of $^{13}$C. Interestingly, the growth of the adducts is dramatically dependent on the trap extraction delay time, and continues to evolve toward larger sizes quite late in the cycle before stabilizing at around 40 ms. This induction time appears to reflect the balance between having sufficiently high pressure in the trap to stop the ions, allow cooling of both the ions and the buffer gas, as well as enable the three-body collisions required for association to occur. The residual pressure in the cell must also be minimized at the time of extraction so that the ions are not destroyed by collision-induced dissociation (CID). It is significant that this can be accomplished given the large driving forces at play in a quadrupole trap (as opposed to the commonly used 22-pole,[39-41] for example). Not surprisingly, condensation requires careful adjustment of the RF voltage and injection energy to minimize collisional heating. Note that the mass ratio of the trapped ions to that of the dominant buffer (He) is about 50, providing a favorable scenario for cooling with minimal translational heating from the drift field. While this scenario is likely not conducive to accurate temperature control of the ions processed in this manner, the application for messenger spectroscopy does not require this feature, and it is straightforward to attach large numbers of $H_2$ molecules to the dianion.

Because the pulsed introduction of the buffer gas used here differs from the continuous scheme employed in the first report of $H_2$ condensation,[31] we also explored the possibility of adding $H_2$ to the singly charged $HOOC(CH_2)_{10}COO^-$ ion. This is a significant test as only the doubly charged system was discussed in that work, suggesting that the adducts were more difficult to form on the singly charged system. FIG. 4 presents the results for the $HOOCCH_2)_{10}COO^-$ anion, and while the extent of solvation is clearly reduced, formation of clusters with up to four $H_2$ molecules are readily observed. This successful tagging of the singly charged anion is quite useful in this study as it provides an excellent opportunity to explore the detailed structural differences between the mono- and dianions by comparing their vibrational spectra.

Spectroscopic Protocols

Vibrational predissociation spectra were obtained for both the singly and doubly charged species by monitoring the evaporative loss of $H_2$ molecules upon resonant excitation:[9, 10]

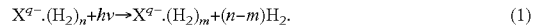

$$X^{q-}\cdot(H_2)_n + h\nu \rightarrow X^{q-}\cdot(H_2)_m + (n-m)H_2. \quad (1)$$

Photoexcitation between 2350-4300 cm$^{-1}$ was carried out using a pulsed, (~7-ns pulse width, 10 Hz) Nd:YAG pumped OPO/OPA laser (LaserVision). The lower-energy range (800-2300 cm$^{-1}$), was generated by parametric mixing of the 3 and 1.5 μm beams in AgGaSe$_2$.[42, 43] The spectra were recorded in the linear action regime determined by following the fluence-dependence of the photodissociation yield, and the raw photofragment signal was normalized for fluctuations in laser pulse energy over the scan. This procedure is necessary to correct for very large changes in output energy of the laser, especially in the lower energy region, but we note that there are still complications in quantitatively comparing the action spectra with the calculated linear absorption spectra due to intrinsic changes in the laser divergence properties over the scan range.

Computational Details

DFT calculations were carried out using the Gaussian 03 package of programs.[7] Geometry optimizations and harmonic frequency calculations of the $^-OOC(CH_2)_{10}COO^-$, $^-OOC(CH_2)_{10}COO^-\cdot H_2$ and $HOOC(CH_2)_{10}COO^-$ ions were carried out using the B3LYP functional and the 6-311++G(d, p) basis set. All harmonic frequency calculations were scaled by 0.956 to bring the calculated C—H stretching fundamentals into agreement with those observed in experimental vibrational spectrum of the dianion. This value is in line with other commonly used scaling factors.[44]

Results and Discussion

Figure 5:
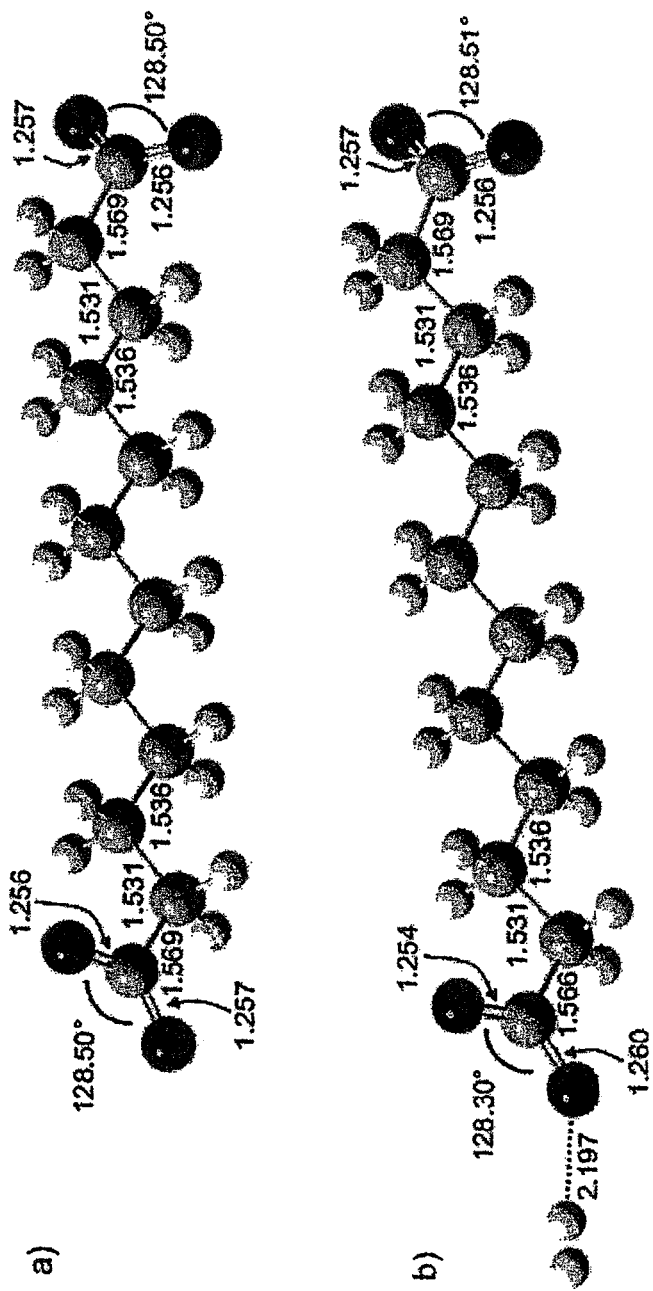
FIG. 5 shows optimized geometries of (a) $^-OOC(CH_2)_{10}COO^-$ and (b) $^-OOC(CH_2)_{10}COO^-$·$H_2$ using the B3LYP functional in conjunction with the 6-311++G(d,p) basis set; selected bond lengths are indicated in angstroms. Note that the addition of $H_2$ causes only minor perturbation of this system (e.g. C=O bond length increases by ~0.003 Å).

Vibrational Predissociation Spectra of the $^-OOC(CH_2)_{10}COO^-\cdot(H_2)_{10}$ Ion The implementation of $H_2$ tagging for vibrational spectroscopy obviously requires that $H_2$ attachment does not significantly perturb the intrinsic spectrum of the target ion. To explore this effect, we carried out electronic structure calculations of the binary $^-OOC(CH_2)_{10}COO^-\cdot H_2$ complex to identify the binding site of, and perturbation induced by $H_2$, with the results presented in FIGS. 5a and 5b for the bare ion and the adduct, respectively. Interestingly, $H_2$ attaches to one of the carboxylate groups where the excess charge is concentrated. The $H_2$ tag has the advantage that, unlike the situation with rare gas tagging, it effectively "reports" on the degree of perturbation through the changes in its characteristic frequency.[13, 21] The vibrational mode of the $H_2$ moiety in the binary complex is calculated (at the harmonic level) to redshift about 250 cm$^{-1}$ relative to the free $H_2$ band, with a concomitant enhancement of the nominally forbidden infrared transition. Comparison of the structures in FIG. 5, however, indicates that $H_2$ indeed does not significantly perturb the equilibrium geometry of the dianion, with bond lengths changing at most by 0.003 Å and the O—C—O angles by less than 0.5°. Here we are primarily concerned with the perturbation of the vibrational spectrum, and the harmonic spectra of the bare ion and the single hydrogen adduct are presented in FIGS. 6a and 6b, respectively, with a comparison of the experimental and calculated frequencies presented in Table 1, FIG. 9. The addition of a single $H_2$ molecule produces slightly nonequivalent $CO_2$ groups, resulting in the calculated frequencies of the two symmetric and asymmetric $CO_2$ stretches to be split by ~5 cm$^{-1}$, considerably smaller than the ~20 cm$^{-1}$ perturbation experimentally observed upon complexation of one $CO_2$ group with $H_2O$.[30]

The abundance pattern observed for the dianion in FIG. 3e displays a maximum yield at around n=10, prompting us to carry out the predissociation survey at this cluster size. The dominant photofragment observed upon resonant excitation of the highest energy CH stretching band at 2929 cm$^{-1}$ corresponded to the loss of 5H$_2$ molecules. This behavior is quite similar to that found for the Ar clusters of many ions, where the extent of the fragmentation is controlled by sequential unimolecular dissociation within the ansatz of an evaporative ensemble.[45, 46] The similarity in photofragmentation properties between Ar and $H_2$ thus indicates that the $H_2$ dissociation energy is also in the neighborhood of 600 cm$^{-1}$. The n=10 parent was selected for the present study because it is prepared in abundance, and the loss of 3-5H$_2$ molecules is readily observed in the second (reflectron) stage of mass selection (as opposed to loss of a single $H_2$, for example, from the mono-adduct).

The $H_2$ predissociation spectrum of the n=10 complex is presented in FIG. 6c. The high energy region was detected via the loss of 5H$_2$ channel, while the lower energy region was monitored by following the loss of 3H$_2$, as anticipated from the binding energy estimate of about 600 cm$^{-1}$ per $H_2$ dissociation. The limited resolution in the secondary (reflectron) TOF analysis stage was actually advantageous in the present experiment as many adjacent loss channels (e.g. n=4, 5, and 6) could be monitored within the same detection window, thus minimizing complications arising from specific channel dependence of the action spectra. The perturbation-induced $H_2$ feature appears centered at 4046 $cm^{-1}$, 112 $cm^{-1}$ to the red of the band origin in the bare molecule,[47] and is interestingly one of the broader features in the spectrum. The shift is, however, even less than the calculated ~250 $cm^{-1}$ value, strongly supporting the suggestion that hydrogen plays an effective role as a messenger to accurately report the spectrum of the ion to which it is attached. The bands associated with the dianion appear at lower energy, and result from the C—H stretches near 2900 $cm^{-1}$, the $CO_2$ stretches next near 1500 $cm^{-1}$ and the $CO_2$ bending mode at 890 $cm^1$. The locations of these features are quite similar to those found in the Kr-tagged suberate dianion.[30] The band contours are consistent with the exclusive formation of the all-trans isomer depicted in FIG. 5a, [see Supplementary Online Materials for other calculated structures] which was identified as the lowest energy form in the photoelectron work of Wang and co-workers on the closely related tetradecanedioic acid dianion;[32] the all-trans motif was also identified as the form of the parent ion in the vibrational spectroscopy study of suberate system.[30]

The $CO_2$ bands are readily assigned to the symmetric and asymmetric stretches at 1345 $cm^{-1}$ and 1611 $cm^{-1}$, respectively, which appear close to the predicted locations, but have relative intensities opposite to that anticipated from the harmonic calculation (FIGS. 6a and 6b). Note that with an even distribution of the $H_2$ molecules attached to each carboxylate (vide infra), the solvent will not break the symmetry of the dianion as was the case in the binary adduct, $^-OOC(CH_2)_{10}COO^-.H_2$. The residual splitting between the two close doublets is quite small in the symmetrical ion, and would not be resolved with the present instrumental resolution of about 2 $cm^{-1}$. In this case, we expect that the four bands derived from the collective in- and out-of-phase motions on each $CO_2$ center will be dominated by the out-of-phase components. Bands derived from the C—H stretches are more complex and appear as a multiplet with clearly distinguishable interlopers on the low energy side of each strong peak. The lowest energy band at 890 $cm^{-1}$ is traced to a mode with dominant contributions from displacements along the O—C—O bend and C—C stretching coordinates, as pointed out earlier by Asmis and co-workers.[30].

The fine structure of the C—H feature is of interest as calculations reveal that it is composed of many closely spaced transitions roughly derived from the symmetric and asymmetric stretches of each contributing methylene group, thus forming a pseudo band structure as this motion delocalizes over the backbone of the aliphatic carbon chain. As a general rule, the collective modes based on the symmetric C—H stretch appear lower in energy and primarily contribute to the peak at 2853 $cm^{-1}$ in the experimental spectrum, while the higher energy features near 2925 $cm^{-1}$ mostly involve the asymmetric stretches. Single transitions contributing most of the intensity are often traced to the $CH_2$ groups closer to the carboxylates and therefore reflect the proximity of the boundary inherent in this finite chain.

Figure 7:
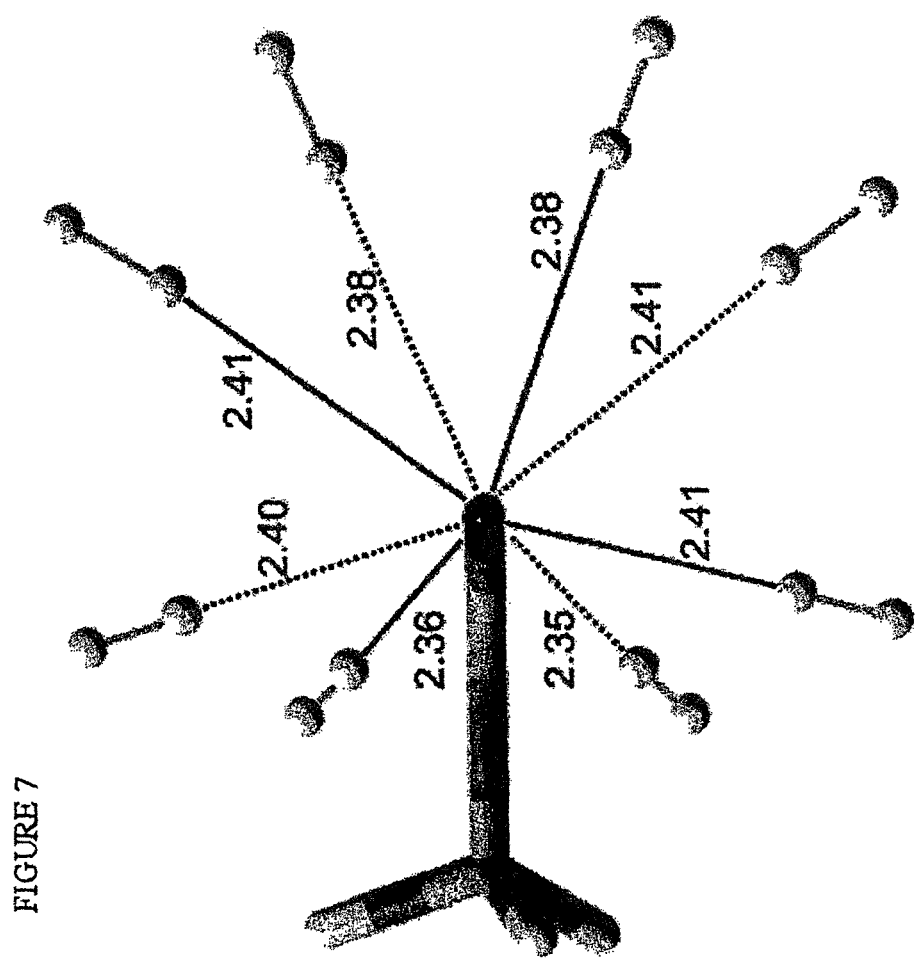
FIG. 7 shows the optimized geometry of the acetate ion solvated by 8H$_2$ molecules, CH$_3$COO$^-$.(H$_2$)$_8$, calculated at the B3LYP/6-311++G(d,p) level of theory. The carboxylate group is surrounded by H$_2$ molecules oriented with their intermolecular axes pointed along the lines originating from each oxygen atom in the carboxylate group. The bond lengths (Å) are indicated in the figure. All of the H$_2$ bond lengths are 0.75 Å, and the solid lines connect to the visible oxygen while the dashed lines originate from the eclipsed oxygen.

Finally, the inventors note that the $H_2$ band centered at 4046 $cm^{-1}$ appears as a nearly symmetrical feature. Given the substantial redshift of the band relative to that in bare $H_2$, one might have anticipated that, with $10H_2$ molecules attached, those closest to the carboxylate oxygens would exhibit the largest shifts, with more remote sites gradually shifting back toward the unperturbed position.[48] The fact that the observed band is homogeneous suggests that many $H_2$ molecules are accommodated in the first solvation shell around each ionic center, and the sharp drop-off at n=16 displayed in FIG. 3e would be consistent with each shell consisting of eight $H_2$ molecules. To gauge the likely packing scenario at play, we carried out a calculation (B3LYP/6-311++G(d,p)) of the simpler $CH_3CO_2^-.(H_2)_8$ cluster, with a minimum energy structure reproduced in FIG. 7. Note that $8H_2$ molecules form a large shell with the $H_2$ molecules standing off almost equidistant from the ion, accounting for the relatively narrow feature in the spectrum. A key aspect of this structure is that the $H_2$ molecules are oriented with their intermolecular axes pointing roughly along the electric field lines radiating away from the excess charge center. Such an arrangement would appear to optimize the pairwise electrostatic interaction to the ion, thus placing the $H_2$ molecules in an unfavorable relative configuration for their mutual attraction.

Vibrational Predissociation Spectrum of $HOOC(CH_2)_{10}COO^-.(H_2)_2$

Because the $H_2$ molecules are not efficiently attached to the singly charged anion, we selected the n=2 parent for the spectroscopic survey to optimize parent intensity and the degree of mass-loss upon photoexcitation, which is especially difficult if only one $H_2$ is lost. The predissociation spectrum of the $HOOC(CH_2)_{10}COO^-.(H_2)_2$ parent is presented in FIG. 8b, which was detected throughout by monitoring the loss of both $H_2$ molecules. The $H_2$ stretch is again clear at the blue edge of the spectrum, but it is interestingly blue-shifted (by 47 $cm^{-1}$) compared to the corresponding band in the dianion complex, bringing it closer to the transition in bare $H_2$. One aspect of the experimental spectrum that is quite clear is that it does not display any features in the vicinity of the free OH, the tell-tale band indicating the presence of the linear isomer. While the absence of a free OH could conceivably result from inefficient energy transfer to the $H_2$ tag from the remote location of the OH group, we note that the previous photoelectron study[34] also concluded that the cyclic form was the only species present in the ion ensemble. In addition, we note that our calculations predict the cyclic form to be more stable than the linear isomer by over 6500 $cm^{-1}$. The inventors therefore proceed to discuss the observed band patterns in the context of the cyclic isomer shown in the inset in FIG. 8c. For example, the formation of the cyclic isomer provides a compelling rationalization for the significant reduction of the redshift displayed by the $H_2$ molecule attached to this species. Specifically, it is reasonable to anticipate that the intramolecular H-bond will concentrate the excess charge on the tethered oxygen atoms, thus reducing the electrostatic perturbation on the $H_2$ ligands, which in turn yields an $H_2$ frequency close to that of the bare molecule.

Figure 8:
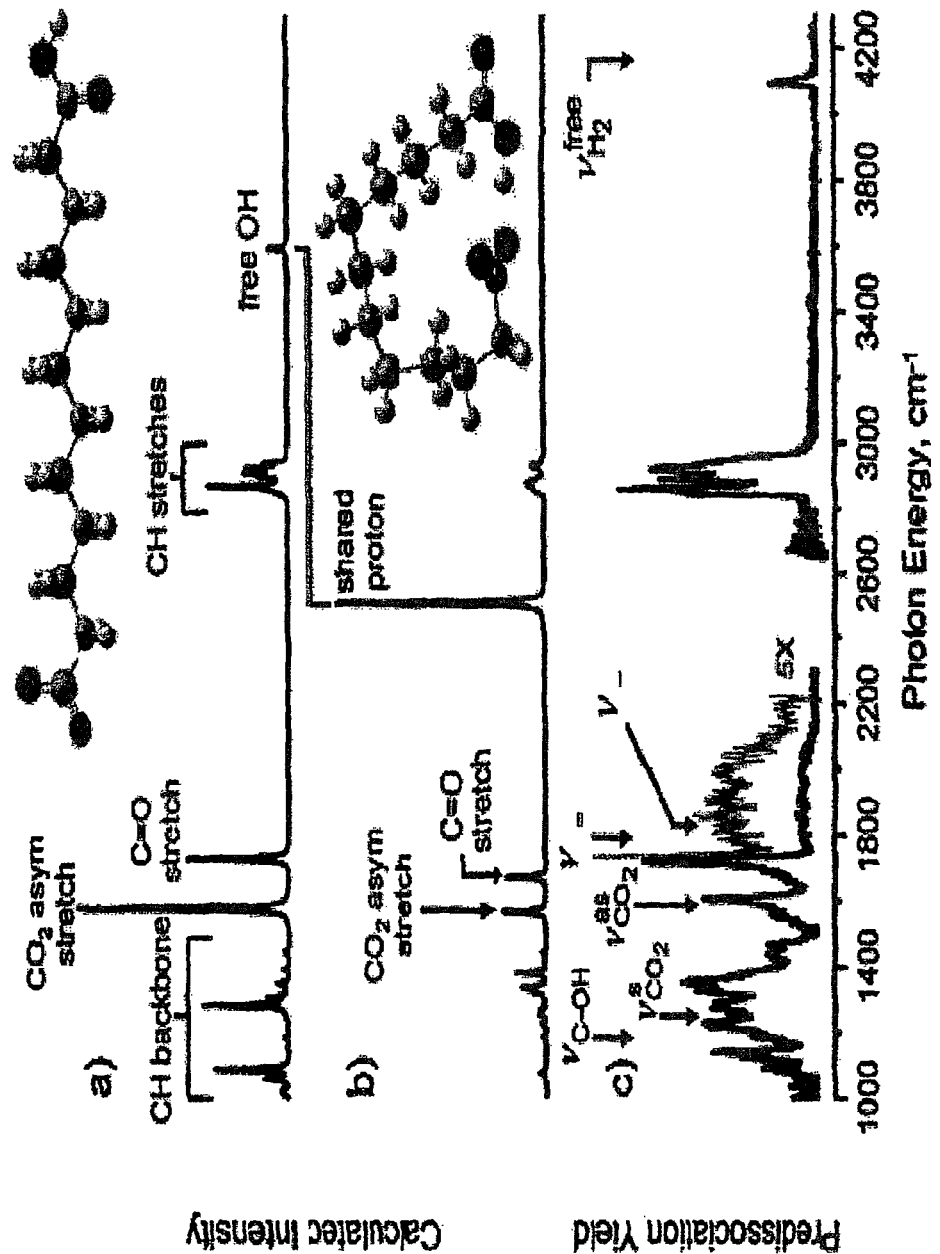
FIG. 8 shows the vibrational predissociation spectra (a) $^-$OOC(CH$_2$)$_{10}$COO$^-$.(H$_2$)$_{10}$ and (b) OOC(CH$_2$)$_{10}$COO$^-$.(H$_2$)$_2$. Band positions of the carboxylate moiety in the dianion are highlighted by arrows in (a), while the positions of the two C—O stretches in neutral acetic acid are highlighted in (b). Calculated harmonic spectra (B3LYP/6-311++G(d,p)) of HOOC(CH$_2$)$_{10}$COO$^-$ for the (c) cyclic and (d) linear isomers. Because of the weak intensity of the band associated with the shared proton, the gray trace in (c) presents an expansion ×5 to facilitate comparison with the experimental spectrum in (b). Calculated frequencies have been scaled by 0.956 as described in the text.

At a qualitative level, it is clear that the low energy (1000-1800 $cm^{-1}$) bands in the monoanion (FIG. 8b) are much more complex than those displayed by the dianion (FIG. 8a). This is anticipated by the harmonic spectrum of the cyclic isomer presented in FIG. 8c, but the inventors note that the strongest calculated band near 2300 $cm^{-1}$, which corresponds to the parallel vibration of the shared proton, is not evident in the experimental spectrum. This is not surprising, however, as the features associated with the bridging proton vibrations are often quite anharmonic,[49] they typically appear strongly mixed with nearby vibrational modes nominally associated with the flanking molecular structures.

Because of the complexity arising from disentangling the features most associated with the shared proton, it is useful to consider how the intramolecular proton bond affects the bands arising from the two carboxylate functionalities effectively linked by the bridging proton. In particular, the structure in FIG. 8c indicates that the ring closes in an asymmetrical fashion such that the bridging proton is located much closer to one of the oxygen atoms (calculated separations are 1.029 and 1.540 Å, respectively). The 2.556 Å calculated distance between the two oxygen atoms bound by the proton is nonetheless quite short, so that the system conforms to a low-barrier H-bond reminiscent of analogous ring structures recently studied by Morton and co-workers.[50]

Perhaps the best indication of the asymmetry in the H-bond can be extracted from behavior of the C=O stretches, which appear relatively isolated in the spectrum near 1600 and 1800 $cm^{-1}$. In the case of the open structure, we would expect to find relatively unperturbed bands associated with the carboxylate moiety (such as those in FIG. 8a), as well as with the neutral carboxylic acid. The latter bands are typically near 1800 $cm^{-1}$ for the C=O stretch and 1200 $cm^{-1}$ for the C—OH stretch, with these asymptotic positions indicated by the arrows in FIG. 8b. The spectrum of the monoanion indeed displays two strong bands in the high energy region expected for the C—O stretches, with one of them falling in essentially the same location as that found for the asymmetric C—O stretch in the dianion (arrows in FIG. 8a). A higher energy feature emerges in the monoanion, however, at 1721 $cm^{-1}$, which falls about 70 $cm^{-1}$ below the expected position for the isolated acid functionality. The asymmetrical intramolecular H-bond in the cyclic motif provides a compelling rationalization for this red-shift, as such behavior would be expected for the C=O nominally on the acid constituent as its proton is partially donated to the carboxylate embedded along the edge of the cyclic structure. The inventors also note that the features assigned to the higher energy C—O stretches in the monoanion appear degraded toward lower energy while those in the open dianion are quite sharp. This effect is likely associated with the mechanics of a strained ring, where the stretching frequencies are highly sensitive to small changes in the intermolecular H-bond. While beyond the scope of this first report, this behavior calls for further study of the monoanions, perhaps exploring the spectral evolution with chain length.

CONCLUSIONS

This example reports the vibrational spectra of the $^-OOC(CH_2)_{10}COO^-$ and $HOOC(CH_2)_{10}COO^-$ ions over the range 800-4300 $cm^{-1}$. The ions were generated by deprotonation of dodecanedioic acid in an electrospray ion source, and the spectra were obtained by predissociation of weakly bound $H_2$ molecules, which were attached to the ions by pulsing a $H_2$/He mixture into a cryogenically cooled ion trap held at a temperature varied over the range 10-20 K. The photofragmentation behavior establishes that the $H_2$ molecules are bound by about 600 $cm^{-1}$, and calculations indicate that $H_2$ induces very little perturbation to the geometries or spectra of the anions to which it is attached. The observed $H_2$ bands fall quite close that that of neutral $H_2$, and are more redshifted when complexed to the doubly charged species than when bound to the singly charged ion. This effect is traced to the formation of an intramolecular H-bonded ring structure in the singly charged form, which acts to disperse the excess charge across the donor and acceptor moieties. The behavior of the C—O stretches suggest that the intramolecular H-bond is asymmetrical, consistent with the calculated minimum energy structure in which the asymmetry in the ring causes the two carboxylate groups to adopt different chemical environments when tethered by a shared proton.

FURTHER EXAMPLES

Reference Set 2 Applies to the Discussion in these Examples

Non-covalent interactions between small molecules and biopolymers mediate many chemical processes ranging from drug action to selective catalysis and provide a fundamental basis for supramolecular chemistry. Identification of the precise atomic-level nature of intermolecular associations is quite difficult, however, because the host-guest complexes are often transient, fluxional species that may not be amenable to unambiguous structural analysis with traditional methods (x-ray, nmr, etc). In the following example, the inventors demonstrate how vibrational spectroscopy according to the present invention can provide this information directly through the frequency changes induced in covalent bonds that are effectively touching at the contact points. These changes can be measured very accurately when the intrinsic vibrational bands are narrow, a situation that becomes available when species are extracted from solution, frozen near 10K in the gas phase, and then spectroscopically analyzed after mass-selection through the predissociation of weakly bound $H_2$ molecules pursuant to the present invention. Resonances closely associated with individual oscillators embedded within a host-guest complex are easily identified through extensive use of site-specific isotopic labeling. The evolution of the various oscillators upon complex formation then reveals the specific linkages in play, which in turn provides a microscopic picture of the docking arrangement. Once constrained in this manner, electronic structure theory can be efficiently used to converge on a unique minimum energy structure within an otherwise computationally prohibitive, high dimensionality landscape.

Figure 10:
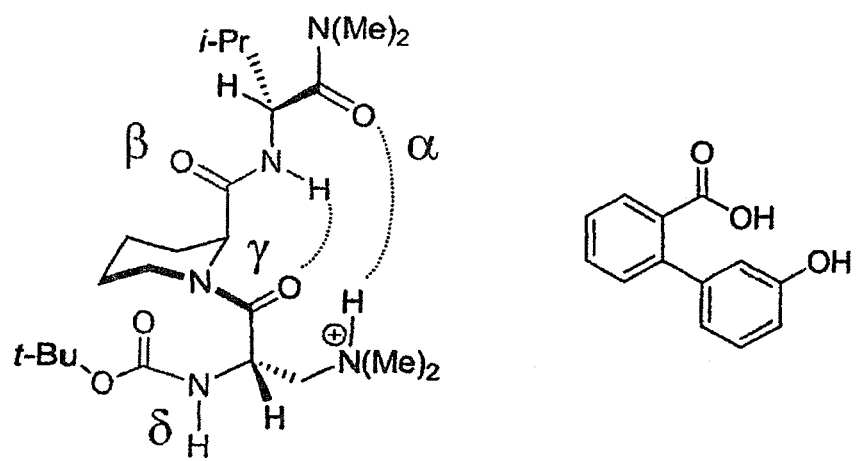
FIG. 10 shows scheme 1 which indicates the structure of the tripeptide host (h), and the biaryl guest molecule (g) to form the protonated variation of the non-covalently bound complex thought to mediate stereoselective bromination of g.[2] See FIG. 10 hereof.

A central strategy in contemporary drug discovery and chemical synthesis involves the design of multiple weak or reversible interactions to achieve selective docking arrangements between complex and yet flexible molecular architectures. Diverse examples include the peptidic interaction motifs underlying antibiotic activity[1] and asymmetric catalysis[2-4] and the field of supramolecular chemistry, most generally. Although simulation plays an increasingly important role in guiding these efforts,[5-8] there is a clear demand for new experimental methods that can probe the host-guest docking geometries of the non-covalently bonded partners. Many of the key attachment points involve complementary H-bonding between C=O, N—H and OH groups, with increasing appreciation for the special role that charged motifs play (e.g., involving —$NH_3^+$ and —$CO_2^-$ as donors and acceptors with neutral partners) in enhancing non-covalent binding.[3,4,9] In favorable cases, x-ray crystal structures or 2D spectroscopies[10-12] can yield this information, but more often the key species occur as transients that are not amenable to these approaches. In these examples, the inventors demonstrate how the cryogenic IR method according to the present invention, carried out after the complexes are formed in solution and isolated using mass spectrometry, can be used to identify the specific C=O and NH groups directly engaged in a binding arrangement. This approach is applied to deduce how a tripeptide host (h), may capture a biaryl guest molecule (g) to form the protonated variation of the non-covalently bound complex thought to mediate stereoselective bromination of g.[2] See FIG. 10 hereof. This complex was chosen as an archetypal example where complimentary multidentate interactions were designed to provide highly selective docking of small molecule to bioactive receptors or potentially floppy catalytic scaffold. In the present case, the attachment motifs are H-bonding in nature, where the —OH groups on g and —NH groups on h provide the donors while the electron lone pairs at the —OH, =O, and —N: sites on both species can act as potential acceptors. In such a scenario, our goal is to elucidate how the guest may dock to the host through experimental determination of the specific acceptor-donor pairs active in complex formation. The elucidation of the structure of ensembles can help contribute to the analysis of possible modes of interaction that may be of significance to functions of interest in processes that depend on intermolecular recognition.

The key advance enabling vibrational spectroscopic characterization of species extracted from solution is the method of the present invention utilizing cryogenic ion processing methods to peptides that were first "tagged" with weakly bound $H_2$ molecules such that single-photon (linear) vibrational action spectra could be generated by following the photoinduced mass loss.[13-15] This method is generally applicable and yields spectra of complex ions and ion-solvent clusters around $10K^{16-18}$ that feature intrinsic linewidths as low as 6 cm$^{-1}$ throughout the fingerprint and X—H stretching regions.[13,14] This spectral simplification arises from the quenching of the flexible scaffolds into a few conformers, each of which exhibit well-resolved vibrational bands when isolated in the gas phase. Such IR spectra are obtained for mass-selected species using a new generation of instruments that integrate mass spectrometry with photofragmentation.[13,17,18]

EXPERIMENTAL

The measurements reported here were carried out in a cryogenic ion photofragmentation spectrometer described previously.[13,14] Briefly, the ions were generated by electrospray ionization[19] of a milimolar solution containing the neutral host h mixture with formic acid ($h_{H+}$) or sodium chloride ($h_{Na+}$) in acetonitrile. The isolation of the host-guest complex ($h_{H+}$-g) presents the challenge of extracting a non-covalently bound assembly from solution and injecting it into the cryogenic spectrometer. This was accomplished by electrospraying a solution containing a 20:1 ratio of g to h and formic acid in acetonitrile, which resulted in recovery of about 30% of the $h_{H+}$-g complex. The ions were guided into an ion trap attached to the second stage of a closed cycle helium cryostat held at 10 K. A short (~1 ms) burst of gas comprised of 20% $D_2$ in a balance of He was carefully introduced in the cell through a pulsed valve to collisionally cool the ions and form $D_2$ adducts. The tagged ions were then extracted into a tandem time-of-flight photofragmentation mass spectrometer. The mass-selected ion packet of interest was photoexcited in the 600-4300 cm$^{-1}$ range using the output of a Nd:YAG pumped OPO/A laser. The infrared spectra were then constructed by monitoring in intensity of the fragment resulting from the single-photon induced evaporation of $D_2$ as a function of the photon energy. The inherent mass-selectivity of this approach is a key advantage because it extracts the catalyst-substrate complex from solution and thus isolates it from the strong background absorptions due to the much more abundant individual components. It is worth noting that this method places unusually high demands on the reproducibility and signal-to-noise performance of the spectrometer, two features that are facilitated by the fact that the predissociation "messenger" technique is carried out in a linear photoexcitation regime.[14]

Results and Discussion

Figure 11:
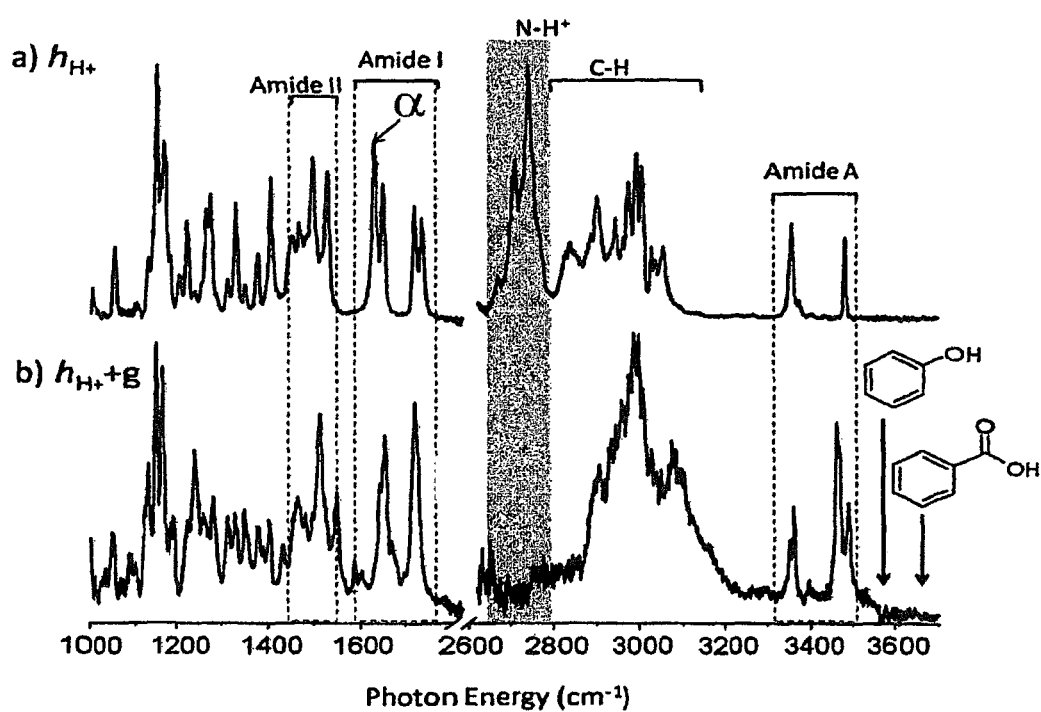
FIG. 11 shows a comparison of the infrared D$_2$-predissociation spectra of (a) h$_{H+}$, and (b) h$_{H+}$-g. The characteristic amides regions discussed in the text are highlighted, along with the location of the intramolecular N—H$^+$ bond in h$_{H+}$

Cryogenic ion spectroscopy has already been applied to the isolated tripeptide host species of interest here ($h_{H+}$), and its vibrational spectrum is reproduced in FIG. 11a. The four important functional groups are denoted by greek letters ($\alpha,\beta,\gamma,\delta$) for reference in the discussion. Four clearly resolved bands appear in the Amide I region (1600-1800 cm$^{-1}$) in addition to two bands in the amide A region (3300-3500 cm$^{-1}$). In the previous study, the intense band near 2700 cm$^{-1}$ was assigned to the NH$^+$ stretch, and its red-shifted position (relative to the free N—H near 3450 cm$^{-1}$) was explained by a strong intramolecular H-bond between N—H+ on the amine and the $\alpha$-C=O group. Another intramolecular H-bond involving the $\gamma$ and $\beta$ Amide groups support the collapsed structure of $h_{H+}$ as indicated in Scheme 1, FIG. 10

FIG. 11b presents the cryogenic ($D_2$-predissociation) vibrational spectrum of the mass-selected $h_{H+}$-g complex central to the present paper, where it can be readily compared with that of the $h_{H+}$. While the $h_{H+}$-g spectrum is clearly more complex, with the exception of the congested region near 3000 cm$^{-1}$, the depth of modulation within the band envelopes indicates that intrinsically narrow lineshapes are retained. Some coarse features of the intermolecular binding arrangement in $h_{H+}$-g are already evident by cursory inspection of its spectrum. For example, the two free OH stretches associated with the isolated biaryl guest (g) are not present in the complex spectrum, indicating that both OH groups of the guest donate H-bonds to the host. Specifically, the free O—H frequency of benzoic acid[20] and phenol[21] are found at 3567 cm$^{-1}$ and 3656 cm$^{-1}$, respectively (arrows at the right of FIG. 1a), significantly above the highest frequency band in the $h_{H+}$-g spectrum at 3487 cm$^{-1}$. In addition, the NH$^+$ feature associated with the intramolecular H-bond in the isolated host is also lost, suggesting that the guest breaks the cyclic motif through formation of intermolecular H-bonds. It is clear, however, based on the relative basicities of the deprotonated host and the guest, that the proton cannot be dislodged from its point of attachment at the tertiary amine in $h_{H+}$. Although more congested, the telltale amide I and amide A regions of the $h_{H+}$-g spectrum are qualitatively similar to those of isolated $h_{H+}$, precluding further structural refinement by analysis of the band pattern alone.

The key to our approach is to identify which Amide groups contribute to the various features in the critical amide I and amide A regions that reveal H-bond activity. This is carried out by leveraging and extending so-called "isotope-edited" infrared spectroscopy in the amide I and amide A regions where it has been extensively used to identify specific interactions in proteins and polypeptides.[10,22-24] In particular, the inventors exploit the fact that single-site isotopic substitution provides a local spectroscopic reporter for the activity of a single bond embedded in a complicated molecular structure. The inventors therefore synthesized individual, isotopically labeled analogs of compounds of interest to our study (See supplementary information for details). When carried out on room temperature samples in solution, these isotope induced shifts are usually only resolved through deconvolutions or by shifting one oscillator clear of the background band using synthetically demanding $^{13}C={}^{18}O$ isotopic substitution.[25-27] The narrow linewidths obtained with the cryogenic ion method used here are quite valuable as the shifts can be easily observed using the simpler $^{13}C$ (or $^{15}N$) incorporation. This approach was successfully demonstrated for the isolated $h_{H+}$ in which incorporation of $^{13}C$ on the $\alpha$ amide (scheme I) allowed the unambiguous assignment of the lowest amide I band (labeled $\alpha$ in FIG. 11a). The amide I frequency shift upon $\alpha$-$^{13}C$ substitution was found to largely reflect displacement of its C=O bond, thus highlighting the local nature of these modes.

Figure 12:
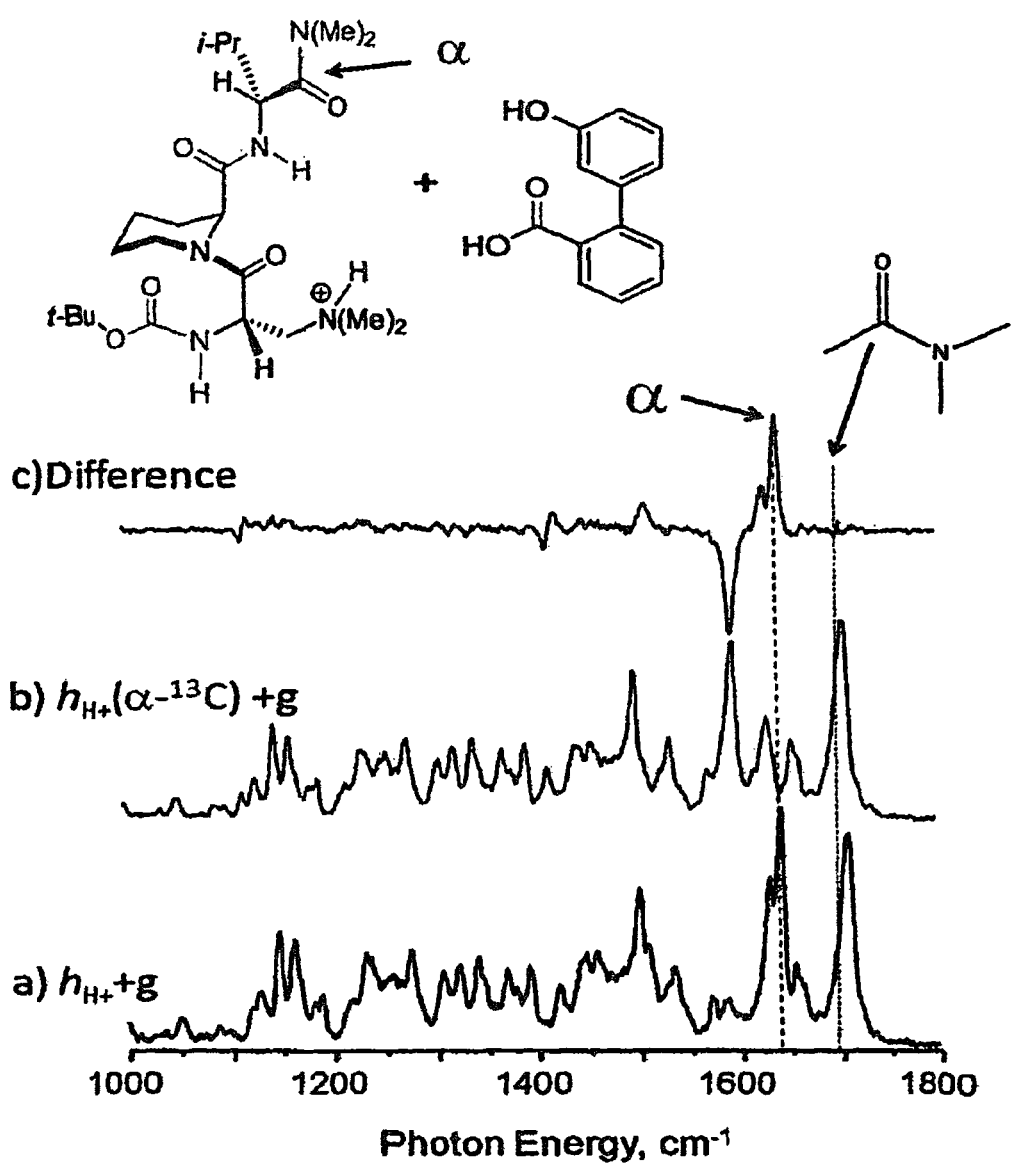
FIG. 12 shows an infrared D$_2$-predissociation spectrum of h$_{H+}$-g with (a) all $^{12}$C and $^{14}$N, (b) α-$^{13}$C. The spectral changes upon isotopic labeling are highlighted in trace (c) which was generated by subtracting traces (b) from (a). The amide I frequency of isolated dimethylacetamide is indicated with an arrow.

To evaluate the efficacy of site-specific isotopic substitution in extracting local information on the binding in the complex environment at play in the $h_{H+}$-g complex, we first carried out a study to monitor the response when the host is labeled in the $\alpha$ position. The resulting spectrum is compared with that from the unlabeled complex in FIG. 12, along with a separate trace (FIG. 12c) displaying subtraction of the two spectra to highlight the extent to which the mass change is registered across the spectrum. Positive going peaks in the difference spectra indicate bands that disappear upon $^{13}$C incorporation while negative peaks reveal the location of the displaced transition, so that the mass affect appears as derivative-type lineshapes when the shift is small. Interestingly, only one strong band in the Amide I region (at 1640 cm$^{-1}$) is significantly shifted, with three minor additional perturbations lower in energy. This effectively isolates the location of the α-C=O stretch from overlapping bands in this region, and verifies that the intrinsic widths of the embedded features are small and that the oscillator strength of most strongly perturbed band (α in FIG. 12c) is primarily derived from the α-C=O. We note that the α-$^{13}$C isotopic substitution clearly reveals the position of a weaker band that was partially overlapping with the α amide I band. The dominant band reveals the frequency of a local C=O oscillator, thus providing a powerful diagnostic for the role of this particular groups in the H-bonding arrangement at play in the complex. Indeed, the 1640 cm$^{-1}$ location of the α-C=O is already informative about its environment, as an isolated (non H-bonded) tertiary amide occurs about 50 cm$^{-1}$ to the blue of the observed feature as indicated by the solid line in FIG. 12. This establishes that, like the situation in the bare host, the $h_{H+}$-g complex involves an H-bond donor to the α-C=O. Since there are many possible donor-acceptor combinations, however, it is necessary to extend the labeling scheme to include as many of the potential binding sites as possible, and to establish whether bands exist that can be attributed to local activity in the scaffold.

Isotope Labeling and Structure of $h_{H+}$

Figure 13:
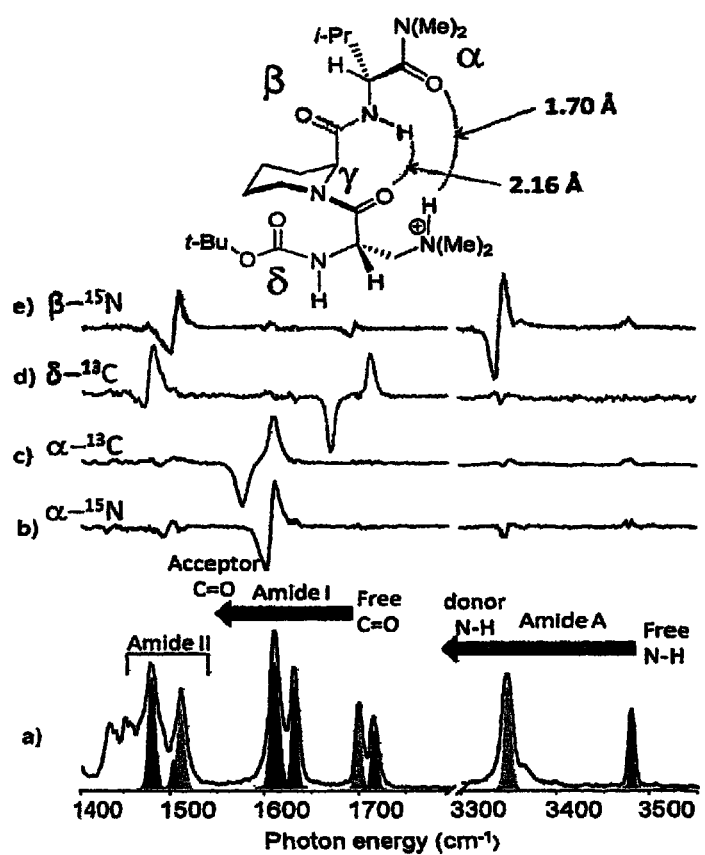
FIG. 13 shows shows a vibrational predissociation spectrum of h$_{H+}$.2D$_2$ with (a) all $^{12}$C and $^{14}$N and (b-e) difference spectra obtained with (b) α-$^{15}$N, (c) α-$^{13}$C, (d)β-$^{15}$N, (e) δ-$^{13}$C. The color coding of the traces and peaks corresponds to the functional groups as indicated in the top schematic structure.

FIG. 13 summarizes the results of site-selective isotope incorporation at four key locations within the four amide groups that comprise the host peptide. The spectral responses were recorded for replacement of the α and β N atoms with $^{15}$N and the α (from before, ref[14]) and δ-C atoms with $^{13}$C. FIG. 13a reproduces the unlabeled $h_{H+}$ spectrum in the amide I/II and A regions for reference. The spectra with heavy isotopes at the indicated positions were subtracted from trace (a) to obtain the color-coded difference spectra in the four upper traces (b-e). (See raw spectra in Fig. S2) Cursory inspection of the subtracted spectra immediately establishes that mass changes at each site contribute to only one or two of the strong transitions. This highlights, once again, the fact that these vibrational modes are all very local oscillators. The various peaks can be assigned to particular amide groups in the context of the cyclic structure of isolated $h_{H+}$ displayed schematically on the top of FIG. 13. These assignments are summarized using the color scheme in FIG. 13a.

The observed locations of the NH donor and C=O acceptor transitions provide a particularly clear picture of the intramolecular interactions that fold the isolated peptide under the conditions of the experiment. The two horizontal color bars depict the transition frequency ranging from non-bonded to fully H-bonded for the amide I and amide A regions. The experimental spectrum is consistent with the $h_{H+}$ structure, shown at the top of FIG. 13, which features two intramolecular H-bonds indicated by the dotted lines, one where the β-N—H (yellow) acts as an H-bond donor and is thus redshifted by ~130 cm$^{-1}$ from the free δ-N—H group (green). The third N—H is associated with the charge center involved in the intramolecular H-bond and appears near 2700 cm$^{-1}$ (N—H$^+$ in FIG. 11a). We can also follow the response of the two H-acceptors, where the carbonyl groups [α(red) and γ(blue)] are found ~85 cm$^{-1}$ lower than the two free carbonyls [δ (green) and β (yellow)]. In this case, the groups engaged in H-bonding are conveniently red-shifted from those that are non-bonded and appear in otherwise clear regions of the spectrum. As such, the lower energy amide I doublet is traced to the two C=O groups accepting H-bonds while two complimentary NH stretches (amide A) are dramatically red shifted relative to the single non-bonded NH group near 3500 cm$^{-1}$.

Although we concentrate here on the mass-dependent affects most useful for structure assignment, we note that the intrinsically collective motions associated with the normal modes underlying the transitions are far more complex. One key feature of particular bands that dominate the response in FIG. 13, however, is that they typically display shifts that approach that expected for the reduced mass change arising from replacement of $^{13}$C or $^{15}$N in a diatomic C=O or N—H bond (36 cm$^{-1}$ and 8 cm$^{-1}$, respectively). Many modes are indeed much more collective in nature and thus less useful for this type of analysis.

Isotope Labeling and Structure of $h_{Na+}$

Having considered the band shifts associated with the intramolecular H-bonds that clamp the isolated peptide, it is a useful exercise to exploit the set of site-labeled variants of the compounds to follow the structural changes when the excess proton is replaced by a positively charged target species with a different interaction profile. The inventors can then follow how the various bands evolve as the host envelopes a simpler target species than the multidentate biaryl guest central to this work. The sodium ion, Na$^+$, provides an excellent candidate as we expect it to strongly favor coordination to one or more of the carbonyls, and the deprotonated host cannot engage in an ionic, intramolecular H-bond largely responsible for its cyclic motif.[28,29]

Figure 14:
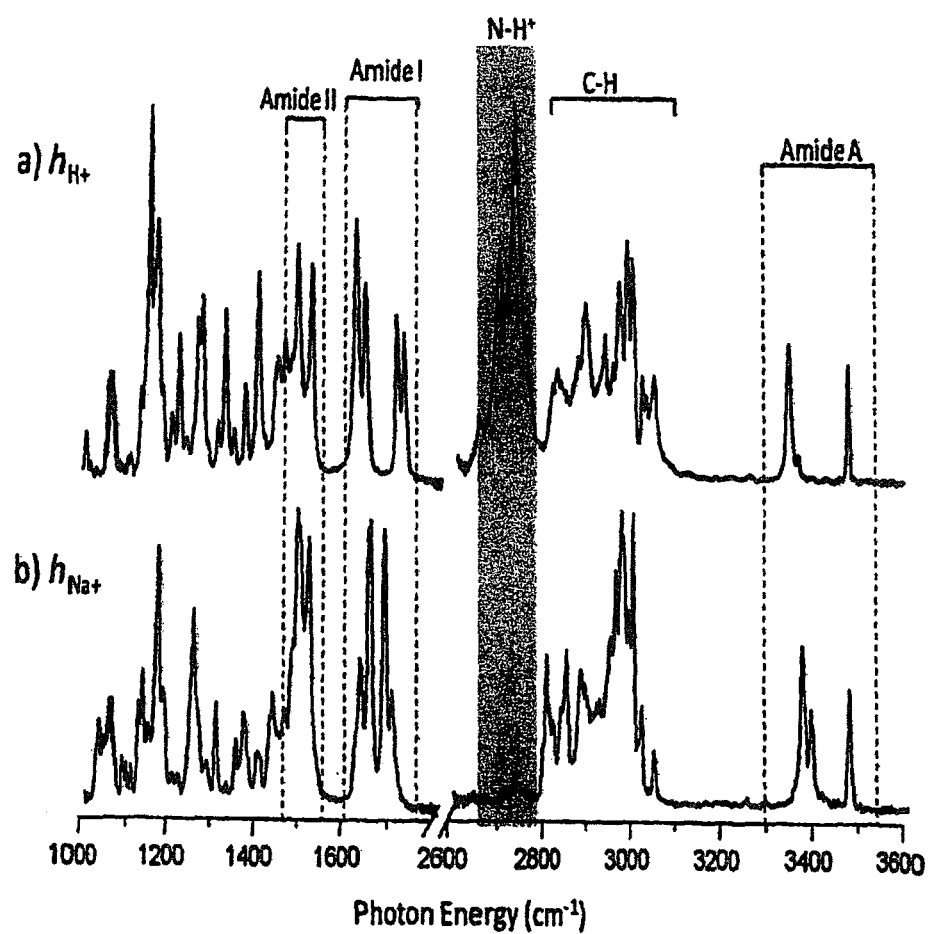
FIG. 14 shows a comparison of the infrared D$_2$-predissociation spectra of (a) h$_{H+}$ and (b) h$_{Na+}$. The characteristic amide regions discussed in the text are highlighted, along with the location of the intramolecular H-bond in h$_{H+}$.

The D$_2$ predissociation spectrum of $h_{Na+}$ is compared with that of $h_{H+}$ in FIG. 14. The most striking qualitative difference is the disappearance of the intense N—H$^+$ band in at 2720 cm$^{-1}$ in the $h_{Na+}$ spectrum, as must occur in absence of the excess proton. The higher frequency amide A bands are similar in the two systems, however, indicating that one of the two NH groups participates in an intramolecular H-bond. The splitting in the H-bonded amide A feature further suggests that either two binding sites are in play or a single site is perturbed by different conformations of more remote groups. The amide I region of $h_{Na+}$ still displays four distinct peaks, but their positions and intensities differ from those in $h_{H+}$ and the entire suite appears more compact and generally centered between the open doublets found in the $h_{H+}$ spectrum.

Figure 15:
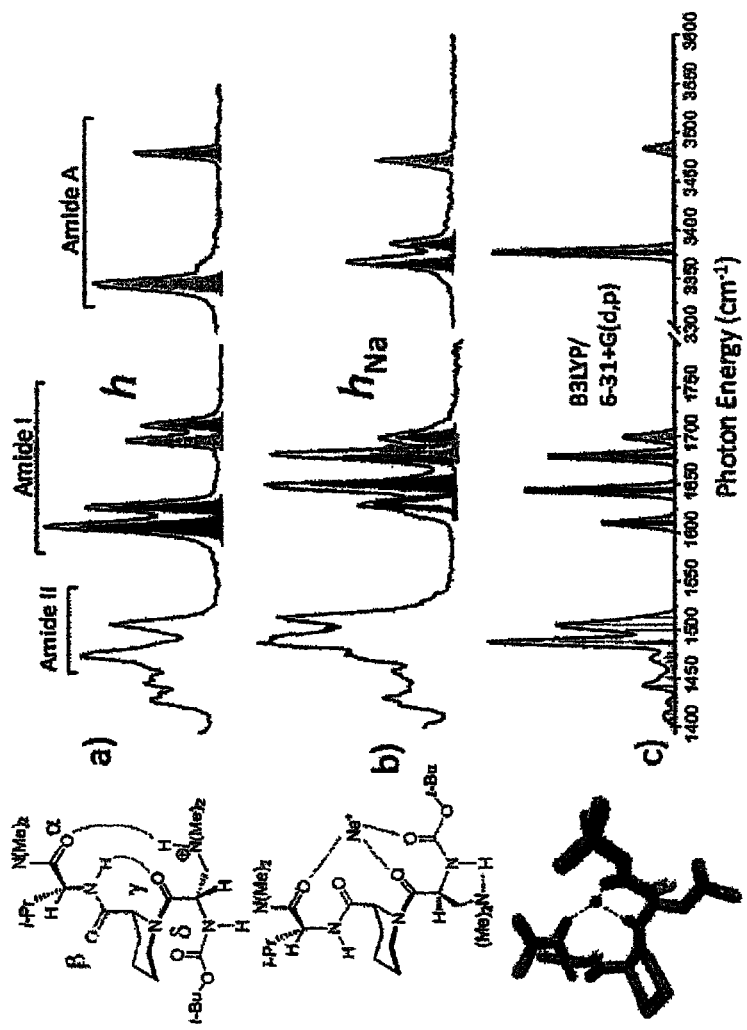
FIG. 15 shows a summary of Amide I and A peak assignments in the a) h$_{H+}$ and b) h$_{Na+}$ infrared spectra. The color coding of the peaks correspond to the functional groups highlighted in the schematic structures on the left. Trace c) presents the calculated harmonic spectra of the lowest energy structure shown in the bottom left corner.

To unravel which constituent within the h groups are active in H-bonding, as well as to establish those coordinated most closely to the ion, we followed the evolution of the various bands using the isotopic shifts of the four sites that were studied in the isolated $h_{H+}$ study (FIG. 13). FIG. 15 compares the resulting positions of the various groups in the $h_{H+}$ and $h_{Na+}$ systems, using the same color scheme as before. Surprisingly, the most striking change going from $h_{H}^+$ to $h_{Na}^+$ occurs in the amide A region where the carriers of the two N—H stretch peaks are exchanged. This change implies a profound rearrangement in which the catalyst attaches to Na$^+$ such that the N—H of the δ amide (green) is now engaged in an internal H-bond while the β-N—H (orange), which is act as a donor in A-H$^+$, is now free. Note that both members of the doublet in the amide A H-bonding region are unambigously traced to the δ amide group.

The evolution of the amide I bands from $h_{H+}$ to $h_{Na+}$ reveals the response of the C=O groups, which are again color-coded according to amide group as indicated on the left. The α band (red), which accepted the strong ionic H-bond from the N—H$^+$ group in $h_{H+}$, blue-shifts by 33 cm$^{-1}$ in $h_{Na+}$ and changes places in energy ordering with the γ band (blue). The doublet structure of the δ amide I contribution (green) is also interesting in light of the doubling of its amide A transition, again suggesting that two closely related conformers are in play. Cis and trans orientations of the t-Bu group are an obvious and compelling assignment for these conformers. The δ-C=O band is red shifted relative to its position in the $h_{H+}$ complex while the β amide I (orange) barely moves. This points to a scenario where three of the C=O groups undergo significant interaction with the ion. These qualitative features of the binding motif provide crucial constraints that focus the computational search for plausible structures into a robust local minimum. The lowest energy form thus obtained is displayed at the left of FIG. 15c and displayed schematically at the left of FIG. 15b to highlight the interactions. Overall, we see that with the loss of the charged intramolecular H-bond in $h_{H+}$, the peptide rearranges its conformation to accommodate the Na$^+$ atom to optimize the more physical (electrostatic) interactions with three of the carbonyls.[28,29] The neutral H-bond evident in the δ amide A region is then traced to the nearby tertiary amine group, while the β NH is rotated free as its C=O group pivots away from the ion.

Isotope Labeling and Structure of $h_{H+}$-g

Figure 16:
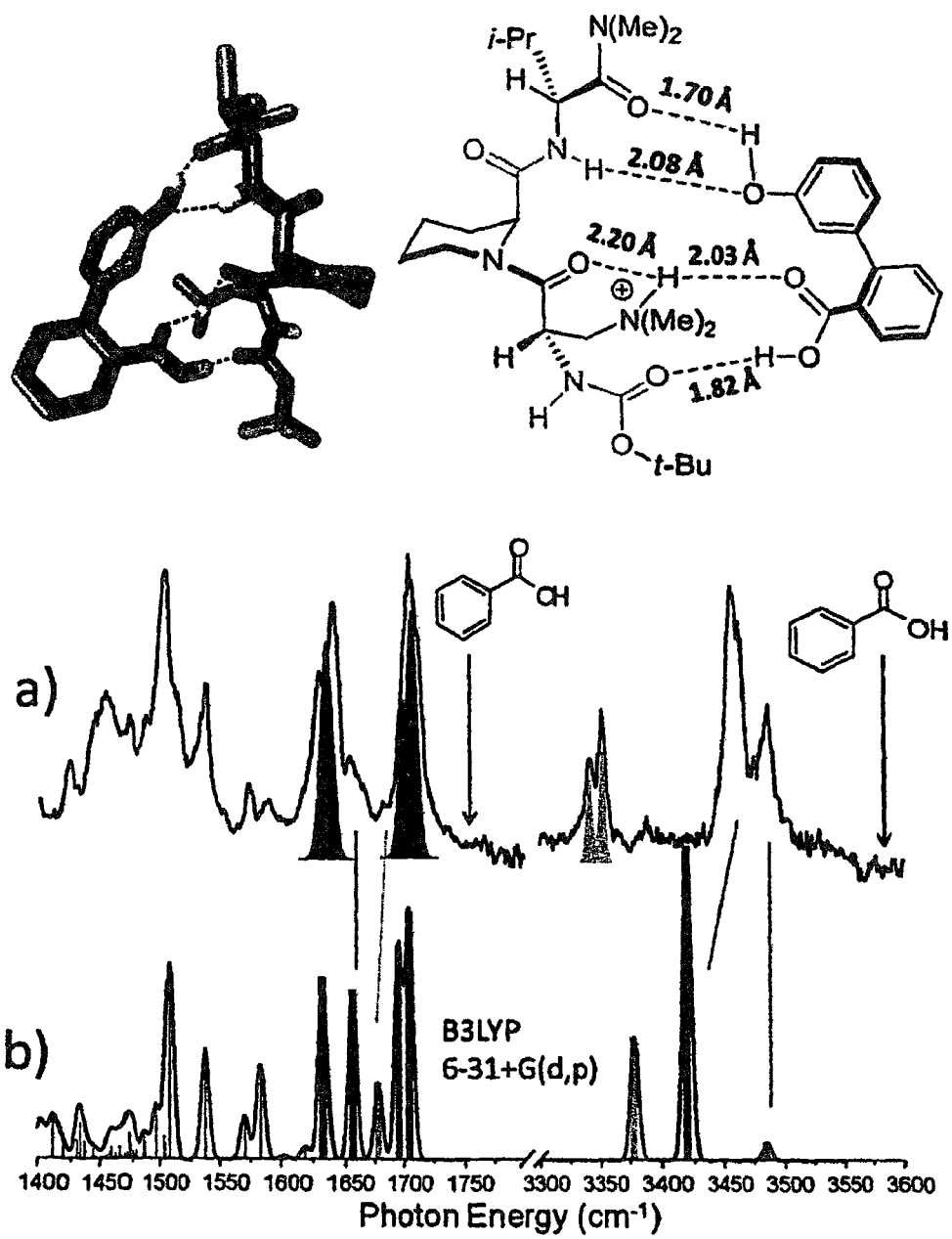
FIG. 16 shows: a) Summary of peak assignments in the h$_{H+}$-g infrared spectra. b) Calculated harmonic spectra of the lowest energy structure shown schematically on top. The color coding of the peaks corresponds to the functional groups highlighted in the schematic structures on top. The characteristic vibrational frequencies of isolated phenol and benzoic acid, used as reference points, are indicated by arrows.

We now turn to the docking motif that tethers the biaryl guest to the peptide scaffold in the non-covalently bound complex, $h_{H+}$-g. The location of the α-C=O resonance and absence of free OH transitions (FIG. 11b) already established that both OH groups on g are engaged in donor H-bonds while the α-C=O is an acceptor. To address the roles of the other potential H-bonding sites, we augment the collection of labeled $h_{H+}$ molecules with a $^{13}$C in the acid group on g. Like the case of the a amide depicted in FIG. 11, all sites yield definitive assignments of bands associated with the NH donors and C=O acceptors, with the results included in the color coded segments of the amide I and A regions in FIG. 16a.

The positions of the g-CO$_2$H based transitions are established in the difference spectrum, and three regions are affected by the heavy isotope. The strongest is actually embedded in the upper range of the amide I envelope at 1704 cm$^{-1}$, and is highlighted in purple in the color-coded spectrum presented in FIG. 16, which again focuses on the Amide signature bands. This acid-based transition falls about 50 cm$^{-1}$ below the 1752 cm$^{-1}$ value reported for isolated benzoic acid (label in FIG. 16),[20,30] indicating that its C=O component is engaged as a strong hydrogen bond acceptor. While this may appear counter-intuitive at first glance, it is in fact typical for organic acids, RCO$_2$H, to share an excess proton between their carbonyl groups in the proton bound binary complexes (RCOH=O—H$^+$—O=COHR').[31,32] This propensity is consistent with the fact that protonation of the bare organic acids occurs preferentially at the C=O to form diol-type arrangements (R—(OH)$_2^+$.

The behavior of the acid functionality on g thus suggests attachment to the positively charged, protonated amine group of $h_{H+}$. This motif must break the cyclic intramolecular H-bond in $h_{H+}$, consistent with the loss of the intense 2720 cm$^{-1}$ N—H$^+$ band and blue shift of the α-C=O (to which the N—H+ was linked) in the $h_{H+}$-g spectrum. Note that when the α-C=O is replaced by —CO$_2$H on g, the NH$^+$ band is expected to blue shift due to the lower basicity of the acid group relative to that of the (α) amide (790.1 kJ/mol vs 877.0 kJ/mol for gas-phase basicity, respectively).[33] The nature of the acid functionality is further defined by the behavior of the weaker bands at lower energy, which probe the motion of the C—OH moiety. The difference spectrum included in Fig. S6 reveals a transition affected by $^{13}$C substitution in the acid group near 1250 cm$^{-1}$. This wide splitting of the two bands associated with —CO$_2$H (1700 cm$^{-1}$ and 1250 cm$^{-1}$ reveals that the basic structure of the acid is intact (i.e., HO—C=O opposed to a salt bridge motif involving —CO$_2^-$), and is therefore acting as a strongly H-bonded domain which both accepts and donates (recall the missing free OH discussed above) an H-bond to the $h_{H+}$ host.

Figure 6:
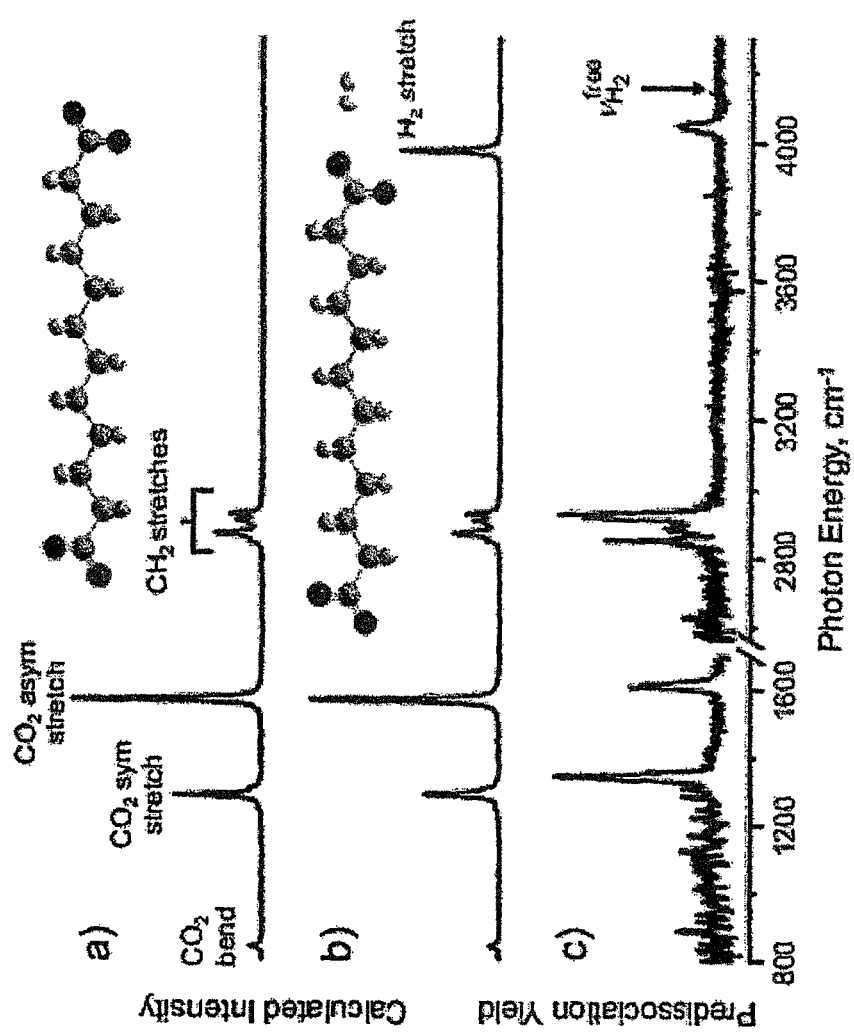
FIG. 6 shows calculated harmonic spectra (B3LYP/6-311++G(d,p)) of (a) $^-OOC(CH_2)_{10}COO^-$ and (b) $^-OOC(CH_2)_{10}COO^-$·$H_2$. Calculated frequencies have been scaled by 0.956 as described in the text. The vibrational predissociation spectrum of (c) $^-OOC(CH_2)_{10}COO^-$·$(H_2)_{10}$ was obtained by monitoring the loss of 5$H_2$ molecules for excitation in the region 2550-4300 cm$^{-1}$ whereas the loss of 3H$_2$ channel was isolated for detection of absorption in the 800-1700 cm$^{-1}$ portion of the spectrum. The frequency of the isolated H$_2$ stretch at 4158 cm$^{-1}$ is indicated by the arrow in (c).

The remaining labeled transitions on the host establish that the β-N—H is involved in H-bonding while the δ-N—H is free, similar to the $h_{H+}$. The δ-C=O (green) is clearly revealed to be redshifted (by 20 cm$^{-1}$) from its uncomplexed position, establishing that it is an H-bond acceptor. Application of these constraints greatly reduces the number of possible $h_{H+}$-g structures, which serves to efficiently guide the ab initio search for minimum energy structures consistent with the empirically deduced H-bonding pattern. The most important clue derives from the assignment of the strongest point of attachment occurring between the protonated amine on $h_{H+}$ and the acid carbonyl on g. Subsequent locking of the two relatively floppy moieties linked by the shared proton then involves only a relatively small number of possibilities, most of which are evident by manipulating physical models. These plausible structures are then readily sorted by the pattern of H-bonding, which reveals the only $h_{H+}$-g structure consistent with the active groups presented in FIG. 6. Of course, many minimizations were carried out using electronic structure theory to identify the locally stable conformation available to the system. Interestingly, the structure in FIG. 6 is indeed the global minimum identified in this computational search, being lower in energy by 0.2 eV (19.3 kJ/mol) relative to the next lower structure. The harmonic spectrum associated with this structure is indicated in FIG. 6b, which is in excellent agreement with the bands assigned by isotopic labeling. As such we propose the assignments of other features not directly pinned down by empirical behavior of the isotopomers by the color coding in FIG. 6b. These predictions provide a solid foundation with which to confirm the structure by further labeling if desired.

One aspect of the study worth mentioning is that, while compelling based on the chemistry involved, the pivotal assignment of the strong contact occurring between NH$^+$ and CO$_2$H is circumstantial. This raises the importance of not only identifying whether particular groups are involved in H-bonding, but also establishing specifically which donors and acceptors are paired, at least in one contact point. In this case, the properties of the ionic H-bond allow assignment of this point with confidence, but such a situation may not always been available. One avenue to explore, therefore, is whether the intensities of both the donor and acceptor bonds can be modulated by the isotopic labeling scheme, which will require H/D substitution. This was not attempted here due to the large number of exchangeable hydrogen atoms, but appears an obvious next step in this method of directly elucidating the host guest interactions using vibrational spectroscopy in the cryogenic regime.

CONCLUSION

This study demonstrates the power and the versatility of the cryogenic ion vibrational spectroscopy technique in resolving the specific non-covalent interactions in multidentate host guest complexes. One of the key aspects of this technique is the ability to isolate transient complexes from the background due to the individual components with the use of electrospray ionization and mass spectrometry. The method yields very highly resolved bands using only microscopic amounts of material typical for mass spectrometric analysis. The central feature is the cooling of the electrosprayed ions from room temperature down to 10K which, in addition to producing the hydrogen-tagged ions, locks the floppy peptides into one or two well defined structures. The cold ions can then be interrogated by infrared vibrational predissociation spectroscopy. The intrinsically sharp transitions underlying congested spectral regions can be revealed through the use of single site isotopic labeling as a powerful tool to unambiguously assign the features associated with each amide group. It then becomes trivial to follow subtle evolutions of the various oscillators upon complex formation which reveals the specific functional groups involved in the non-covalent linkages. The overall strategy yields a microscopic picture of a docking arrangement, which highly constrains the possible structures so that electronic structure theory can be efficiently used to converge on a unique minimum energy structure within an otherwise computationally prohibitive, high dimensionality landscape. The method appears general and likely to become a central tool in the arsenal of chemical analysis available to characterize not only reaction products but also intermediates along the pathways of multistep catalytic reactions, and other processes that depend on supramolecular associations.

REFERENCES

First Set

[1] M. F. Bush, R. J. Saykally, E. R. Williams, Evidence for Water Rings in the Hexahydrated Sulfate Dianion from IR Spectroscopy, J. Am. Chem. Soc. 129 (2007) 2220-2221.

[2] K. Rajabi, K. Theel, E. A. L. Gillis, G. Beran, T. D. Fridgen, The Structure of the Protonated Adenine Dimer by Infrared Multiple Photon Dissociation Spectroscopy and Electronic Structure Calculations, J. Phys. Chem. A 113 (2009) 8099-8107.

[3] R. C. Dunbar, D. T. Moore, J. Oomens, IR spectroscopic characterization of intermediates in a gas-phase ionic reaction: The decarbonylation of $Co^+$ (acetophenone), Int. J. Mass Spectrom. 265 (2007) 182-186.

[4] D. R. Carl, T. E. Cooper, J. Oomens, J. D. Steill, P. B. Armentrout, Infrared multiple photon dissociation spectroscopy of cationized methionine: effects of alkali-metal cation size on gas-phase conformation, Phys. Chem. Chem. Phys. 12 (2010) 3384-3398.

[5] C. M. Leavitt, J. Oomens, R. P. Dain, J. Steill, G. S. Groenewold, M. J. V. Stipdonk, IRMPD Spectroscopy of Anionic Group II Metal Nitrate Cluster Ions, J. Am. Soc. Mass Spectrom. 20 (2009) 772-782.

[6] L. Jiang, T. Wende, R. Bergmann, G. Meijer, K. R. Asmis, Gas-Phase Vibrational Spectroscopy of Microhydrated Magnesium Nitrate Ions $[MgNO_3(H_2O)_{1-4}]^+$, J. Am. Chem. Soc. 132 (2010) 7398-7404.

[7] M. J. Frisch, G. W. Trucks, H. B. Schlegel, G. E. Scuseria, M. A. Robb, J. R. Cheeseman, J. J. A. Montgomery, T. Vreven, K. N. Kudin, J. C. Burant, J. M. Millam, S. S. Iyengar, J. Tomasi, V. Barone, B. Mennucci, M. Cossi, G. Scalmani, N. Rega, G. A. Petersson, H. Nakatsuji, M. Hada, M. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. Dannenberg, V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui, A. G. Baboul, S. Clifford, J. Cioslowski, B. B. Stefanov, G. Liu, A. Liashenko, P. Piskorz, I. Komaromi, R. L. Martin, D. J. Fox, T. Keith, M. A. Al-Laham, C. Y. Peng, A. Nanayakkara, M. Challacombe, P. M. W. Gill, B. Johnson, W. Chen, M. W. Wong, C. Gonzalez, J. A. Pople, in, 2004 Gaussian, Inc., Wallingford, Conn.

[8] T. S. Zwier, Laser probes of conformational isomerization in flexible molecules and complexes, J. Phys. Chem. A 110 (2006) 4133-4150.

[9] M. A. Johnson, Vibrational Predissociation Ion Spectroscopy, Encyclopedia of Mass Spectrometry Vol. 5 (2002).

[10] M. Okumura, L. I. Yeh, J. D. Myers, Y. T. Lee, Infrared spectra of the cluster ions $H_7O_3^+.H_2$ and $H_9O_4^+.H_2$, J. Chem. Phys. 85 (1986) 2328-2329.

[11] T. Pankewitz, A. Lagutschenkov, G. Niedner-Schatteburg, S. S. Xantheas, Y. T. Lee, Infrared spectrum of $NH_4^+$ $(H_2O)$: Evidence for mode specific fragmentation, J. Chem. Phys. 126 (2007) 074307.

[12] D. A. Wild, P. S. Weiser, E. J. Bieske, A. Zehnacker, The $^{35}Cl^-$—$H_2$ and $^{35}Cl^-$-$D_2$ anion complexes: Infrared spectra and radial intermolecular potentials, J. Chem. Phys. 115 (2001) 824-832.

[13] C. Emmeluth, B. L. J. Poad, C. D. Thompson, G. H. Weddle, E. J. Bieske, Infrared spectra of the $Li^+.(H_2)_n$ (n=1-3) cation complexes, J. Chem. Phys. 126 (2007) 204309.

[14] N. Solca, O. Dopfer, Microsolvation of the Phenol Cation ($Ph^+$) in Nonpolar Environments: Infrared Spectra of $Ph^+.L_n$ (L=He, Ne, Ar, $N_2$, $CH_4$), J. Phys. Chem. A 105 (2001) 5637-5645.

[15] N. Solca, O. Dopfer, Protonated benzene: IR spectrum and structure of $C_6H_7^+$, Angew. Chem. Int. Ed. 41 (2002) 3628-3631.

[16] P. D. Carnegie, A. B. McCoy, M. A. Duncan, IR Spectroscopy and Theory of $Cu^+(H_2O)Ar_2$ and $Cu^+(D_2O)Ar_2$ in the O—H(O-D) Stretching Region: Fundamentals and Combination Bands, J. Phys. Chem. A 113 (2009) 4849-4854.

[17] G. E. Douberly, A. M. Ricks, P. v. R. Schleyer, M. A. Duncan, Infrared spectroscopy of gas phase $C_3H_5^+$: The allyl and 2-propenyl cations, J. Phys. Chem. 128 (2008) 021102/021101-021102/021104.

[18] A. Fujii, T. Sawamura, S. Tanabe, T. Ebata, N. Mikami, Infrared Dissociation Spectroscopy of the OH Stretching Vibration of Phenol Rare-Gas Van-der-Waals Cluster Ions, Chem. Phys. Lett. 225 (1994) 104-107.

[19] A. Fujii, E. Fujimaki, T. Ebata, N. Mikami, Infrared spectroscopy of CH stretching vibrations of jet-cooled alkylbenzene cations by using the "messenger" technique, J. Chem. Phys. 112 (2000) 6275-6284.

[20] Y. Inokuchi, R. Matsushima, Y. Kobayashi, T. Ebata, Ion core structure in $(N_2O)_n^+$ (n=2-8) studied by infrared photodissociation spectroscopy, J. Chem. Phys. 131 (2009) 044325.

[21] M. Okumura, L. I. Yeh, J. D. Myers, Y. T. Lee, Infrared-spectra of the solvated hydronium ion-vibrational predissociation spectroscopy of mass-selected $H_3O^+.(H_2O)_N.$ $(H_2)_M$, J. Phys. Chem. 94 (1990) 3416-3427.

[22] M. Okumura, L. I. Yeh, Y. T. Lee, Infrared-Spectroscopy of the Cluster Ions $H_3^+.(H_2)_N$, J. Chem. Phys. 88 (1988) 79-91.

[23] T. D. Vaden, B. Forinash, J. M. Lisy, Rotational structure in the asymmetric OH stretch of $Cs^+.(H_2O)Ar$, J. Chem. Phys. 117 (2002) 4628-4631.

[24] D. J. Miller, J. M. Lisy, Hydrated Alkali-Metal Cations: Infrared Spectroscopy and ab Initio Calculations of $M^+$ $(H_2O)_{x=2-5}Ar$ cluster ions for M=Li, Na, K, and Cs, J. Am. Chem. Soc. 130 (2008) 15381-15392.

[25] R. A. Relph, T. L. Guasco, B. M. Elliott, M. Z. Kamrath, A. B. McCoy, R. P. Steele, D. P. Schofield, K. D. Jordan, A.

A. Viggiano, E. E. Ferguson, M. A. Johnson, How the Shape of an H-bonded Network Controls Proton-Coupled Water Activation in HONO formation, Science 327 (2010) 308-312.

[26] S. G. Olesen, T. L. Gausco, G. H. Weddle, S. Hammerum, M. A. Johnson, Vibrational predissociation spectra of the Ar-tagged [$CH_4 \cdot H_3O^+$] binary complex: spectroscopic signature of hydrogen bonding to an alkane, Mol. Phys. 108 (2010) 1191-1197.

[27] H. Schneider, K. M. Vogelhuber, F. Schinle, J. M. Weber, Aromatic molecules in anion recognition: Electrostatics versus H-bonding, J. Am. Chem. Soc. 129 (2007) 13022-13026.

[28] H. Schneider, K. M. Vogelhuber, J. M. Weber, Infrared spectroscopy of anionic hydrated fluorobenzenes, J. Chem. Phys. 127 (2007) 114311.

[29] N. L. Pivonka, C. Kaposta, M. Brummer, G. von Helden, G. Meijer, L. Woste, D. M. Neumark, K. R. Asmis, Probing a strong hydrogen bond with infrared spectroscopy: Vibrational predissociation of $BrHBr^-\cdot Ar$, J. Chem. Phys. 118 (2003) 5275-5278.

[30] D. J. Goebbert, T. Wende, R. Bergmann, G. Meijer, K. R. Asmis, Messenger-Tagging Electrosprayed Ions: Vibrational Spectroscopy of Suberate Dianions, J. Phys. Chem. A 113 (2009) 5874-5880.

[31] X. B. Wang, L. S. Wang, Development of a low-temperature photoelectron spectroscopy instrument using an electrospray ion source and a cryogenically controlled ion trap, Rev. Sci. Instrum. 79 (2008) 073108-073101-073108.

[32] X. B. Wang, X. P. Xing, L. S. Wang, Observation of $H_2$ Aggregation onto a Doubly Charged Anion in a Temperature-Controlled Ion Trap, J. Phys. Chem. A 112 (2008) 13271-13274.

[33] J. M. Headrick, J. C. Bopp, M. A. Johnson, Predissociation spectroscopy of the argon-solvated $H_5O_2^+$ "Zundel" cation in the 1000-1900 $cm^{-1}$ region, J. Chem. Phys. 121 (2004) 11523-11526.

[34] H. K. Woo, X. B. Wang, K. C. Lau, L. S. Wang, Low-Temperature Photoelectron Spectroscopy of Aliphatic Dicarboxylate Monoanions, $HO_2C(CH_2)_nCO_2^-$ (n=1-10): Hydrogen Bond Induced Cyclization and Strain Energies, J. Phys. Chem. A 110 (2006) 7801-7805.

[35] L. A. Posey, M. A. Johnson, Photochemistry of hydrated electron clusters $(H_2O)_n^-$ ($15 \le n \le 40$) at 1064 nm: Size-dependent competition between photofragmentation and photodetachment, J. Chem. Phys. 89 (1988) 4807-4814.

[36] M. A. Johnson, W. C. Lineberger, Pulsed Methods for Cluster Ion Spectroscopy, in Techniques for the Study of Ion-Molecule Reactions, in Farrar, J. M., and Saunders, W. H., Jr., (Eds.), Wiley, New York, 1988, p. 591.

[37] P. B. O'Connor, C. E. Costello, W. E. Earle, A high voltage RF oscillator for driving multipole ion guides, J. Am. Soc. Mass Spectrom. 13 (2002) 1370-1375.

[38] R. Mathur, P. B. O'Connor, Design and implementation of a high power rf oscillator on a printed circuit board for multipole ion guides, Review of Scientific Instruments 77 (2006)-.

[39] D. Gerlich, Ion-Neutral Collisions in a 22-Pole Trap at Very-Low Energies, Phys. Scripta T59 (1995) 256-263.

[40] D. Gerlich, Inhomogeneous RF-Fields—A Versatile Tool for the Study of Processes with Slow Ions, Adv. Chem. Phys. 82 (1992) 1-176.

[41] O. V. Boyarkin, S. R. Mercier, A. Kamariotis, T. R. Rizzo, Electronic Spectroscopy of cold, protonated tryptophan and tyrosine, J. Am. Chem. Soc. 128 (2006) 2816-2817.

[42] M. Gerhards, C. Unterberg, A. Gerlach, Structure of a beta-sheet model system in the gas phase: Analysis of the C=O stretching vibrations, Phys. Chem. Chem. Phys. 4 (2002) 5563-5565.

[43] J. A. Stearns, A. Das, T. S. Zwier, Hydrogen atom dislocation in the excited state of anthranilic acid: probing the carbonyl stretch fundamental and the effects of water complexation, Phys. Chem. Chem. Phys. 6 (2004) 2605-2610.

[44] N. S. R. D. N. NIST Computational Chemistry Comparision and Benchmark Database, Release 15a, April 2010, Editor: Russell D. Johnson III, http://cccbdb.nist.gov/, in.

[45] P. J. Campagnola, L. A. Posey, M. A. Johnson, Controlling the internal energy content of size-selected cluster ions: An experimental comparison of the metastable decay rate and photofragmentation methods of quantifying the internal excitation of $(H_2O)_n^-$, J. Chem. Phys. 95 (1991) 7998-8004.

[46] W. H. Robertson, J. A. Kelley, M. A. Johnson, A pulsed supersonic entrainment reactor for the rational preparation of cold ionic complexes, Rev. Sci. Instrum. 71 (2000) 4431-4434.

[47] K. P. Huber, G. Herzberg, Molecular Spectra and Molecular Structure: IV. Constants of Diatomic Molecules, ed., Van Nostrand Reinhold Company, New York 1979.

[48] M. A. Duncan, Infrared spectroscopy to probe structure and dynamics in metal ion-molecule complexes, Int. Rev. Phys. Chem. 22 (2003) 407-435.

[49] J. R. Roscioli, L. R. McCunn, M. A. Johnson, Quantum Structure of the Intermolecular Proton Bond, Science 316 (2007) 249-254.

[50] S. Yaghmaei, S. Khodagholian, J. M. Kaiser, F. S. Tham, L. J. Mueller, T. H. Morton, Chelation of a proton by an aliphatic tertiary diamine, J. Am. Chem. Soc. 130 (2008) 7836.

REFERENCES

Second Set (1) Williams, D. H.; Bardsley, B. *Angew Chem Int Edit* 1999, 38, 1173-1193.

(2) Gustafson, J. L.; Lim, D.; Miller, S. J. *Science* 2010, 328, 1251-1255.

(3) Taylor, M. S.; Jacobsen, E. N. *Angew. Chem. Int. Edit.* 2006, 45, 1520-1543.

(4) Jacobsen, E. N.; Doyle, A. G. *Chem. Rev.* 2007, 107, 5713-5743.

(5) Bleicher, K. H.; Bohm, H. J.; Muller, K.; Alanine, A. I. *Nat. Rev. Drug Discovery* 2003, 2, 369-378.

(6) Bajorath, F. *Nat. Rev. Drug Discovery* 2002, 1, 882-894.

(7) Jorgensen, W. L. *Science* 2004, 303, 1813-1818.

(8) Shoichet, B. K. *Nature* 2004, 432, 862-865.

(9) Prins, L. J.; Reinhoudt, D. N.; Timmerman, P. *Angew. Chem. Int. Edit.* 2001, 40, 2382-2426.

(10) Ham, S.; Cha, S.; Choi, J. H.; Cho, M. *J. Chem. Phys.* 2003, 119, 1451-1461.

(11) Perrin, C. L.; Nielson, J. B. *Annu. Rev. Phys. Chem.* 1997, 48, 511-544.

(12) Jeffrey, G. A.; Saenger, W. *Hydrogen bonding in biological structures*; Springer-Verlag: Berlin; N.Y., 1991.

(13) Kamrath, M. Z.; Relph, R. A.; Guasco, T. L.; Leavitt, C. M.; Johnson, M. A. *Int. J Mass Spec.* 2011, 300, 91-98.

(14) Kamrath, M. Z.; Garand, E.; Jordan, P. A.; Leavitt, C. M.; Wolk, A. B.; Van Stipdonk, M. J.; Miller, S. J.; Johnson, M. A. *J. Am. Chem. Soc.* 2011, 133, 6440-6448.

(15) Okumura, M.; Yeh, L. I.; Myers, J. D.; Lee, Y. T. *J. Chem. Phys.* 1986, 85, 2328-2329.
(16) Stearns, J. A.; Mercier, S.; Seaiby, C.; Guidi, M.; Boyarkin, O. V.; Rizzo, T. R. *J. Am. Chem. Soc.* 2007, 129, 11814-11820.
(17) Rizzo, T. R.; Stearns, J. A.; Boyarkin, O. V. *Int. Rev. Phys. Chem.* 2009, 28, 481-515.
(18) Goebbert, D. J.; Wende, T.; Bergmann, R.; Meijer, G.; Asmis, K. R. *J. Phys. Chem. A* 2009, 113, 5874-5880.
(19) Fenn, J. B.; Mann, M.; Meng, C. K.; Wong, S. F.; Whitehouse, C. M. *Science* 1989, 246, 64-71.
(20) Stepanian, S. G.; Reva, I. D.; Radchenko, E. D.; Sheina, G. G. *Vib. Spectrosc.* 1996, 11, 123-133.
(21) Ishiuchi, S.; Shitomi, H.; Takazawa, K.; Fujii, M. *Chem. Phys. Lett.* 1998, 283, 243-250.
(22) Tadesse, L.; Nazarbaghi, R.; Walters, L. *J. Am. Chem. Soc.* 1991, 113, 7036-7037.
(23) Haris, P. I.; Robillard, G. T.; Vandijk, A. A.; Chapman, D. *Biochemistry* 1992, 31, 6279-6284.
(24) Sonar, S.; Lee, C. P.; Coleman, M.; Patel, N.; Liu, X. M.; Marti, T.; Khorana, H. G.; Rajbhandary, U. L.; Rothschild, K. J. *Nat. Struct. Biol.* 1994, 1, 512-517.
(25) Lin, Y. S.; Shorb, J. M.; Mukherjee, P.; Zanni, M. T.; Skinner, J. L. *J. Phys. Chem. B* 2009, 113, 592-602.
(26) Hochstrasser, R. M.; Fang, C.; Wang, J.; Charnley, A. K.; Barber-Armstrong, W.; Smith, A. B.; Decatur, S. M. *Chem. Phys. Lett.* 2003, 382, 586-592.
(27) Arkin, I. T.; Torres, J.; Adams, P. D. *J. Mol. Biol.* 2000, 300, 677-685.
(28) Ohanessian, G.; Semrouni, D.; Balaj, O. P.; Calvo, F.; Correia, C. F.; Clavaguera, C. *J. Am. Soc. Mass Spectrom.* 2010, 21, 728-738.
(29) Dunbar, R. C.; Steill, J. D.; Oomens, J. *Int. J. Mass Spectrom.* 2010, 297, 107-115.
(30) Bakker, J. M.; Mac Aleese, L.; von Helden, G.; Meijer, G. *J. Chem. Phys.* 2003, 119, 11180-11185.
(31) Inokuchi, Y.; Nishi, N. *J. Phys. Chem. A* 2003, 107, 11319-11323.
(32) Kim, K. S.; Lee, H. M.; Kumar, A.; Kolaski, M.; Kim, D. Y.; Lee, E. C.; Min, S. K.; Park, M.; Choi, Y. C. *Physical Chemistry Chemical Physics* 2010, 12, 6278-6287.
(33) Hunter, E. P. L.; Lias, S. G. *J. Phys. Chem. Ref. Data* 1998, 27, 413-656.

The invention claimed is:

1. A method for producing gas-ion adducts in a low temperature controlled ion trap of a mass spectrometry apparatus comprising exposing resident ions of interest in said ion trap at low temperature to a complexing gas or gas mixture which is pulsed into said ion trap, and allowing said ions of interest and said pulsed gas or gas mixture to form gas-ion adducts which are subjected to mass spectrometry analysis and optionally, at least one analysis selected from infra red (vibrational) spectroscopy, UV (ultraviolet) analysis and visible spectrum analysis, wherein said complexing gas or gas mixture is selected from the group consisting of a mixture of hydrogen and helium, argon (Ar), neon (Ne), krypton (Kr), xenon (Xe), carbon dioxide ($CO_2$), carbon monoxide (CO), nitrogen ($N_2$), methane ($CH_4$), and sulfur hexafluoride ($SF_6$).

2. The method according to claim 1 wherein said gas-ion adduct is subjected to mass spectrometry and vibration (IR) spectroscopy.

3. The method according to claim 1 wherein said low temperature controlled ion trap is temperature controlled to no higher than about 50 degrees Kelvin.

4. The method according to claim 2 wherein said low temperature controlled ion trap is temperature controlled to no higher than about 20 degrees Kelvin.

5. The method according to claim 1 wherein said low temperature controlled ion trap is temperature controlled to no higher than about 10 degrees Kelvin.

6. The method according to claim 1 wherein said gas mixture is a mixture of hydrogen and helium in a ratio (V:V) of about 20:80.

7. The method according to claim 6 wherein said complexing gas mixture is pulsed into said ion trap at a temperature ranging from about 10 degrees Kelvin to above ambient temperature.

8. The method according to claim 6 wherein said complexing gas mixture is pulsed into said ion trap at a temperature about 10 degrees below or above ambient air temperature.

9. The method according to claim 6 wherein said complexing gas mixture is pulsed into said ion trap at a temperature of about ambient air temperature.

10. The method according to claim 1 wherein said gas or gas mixture is pulsed into said ion trap for a period ranging from less than 1 about millisecond to about 100 milliseconds at intervals ranging from about 1 millisecond to about 100 milliseconds.

11. The method according to claim 10 wherein said gas or gas mixture is pulsed into said ion trap for a period ranging from about 1 millisecond to about 100 milliseconds.

12. The method according to claim 11 wherein said gas or gas mixture is pulsed into said ion trap for a period ranging from about 70 to about 90 milliseconds.

13. The method according to claim 1 wherein said ion trap is selected from the group consisting of a Penning trap, a Paul trap (quadrupole ion trap) and multipole trap.

14. The method according to claim 1 wherein said ion trap is a Paul trap.

15. The method according to claim 1 wherein said gas-ion adducts are purified by extraction after exiting from said ion trap.

16. A method for identifying and/or characterizing ions prepared from sample compounds in a low temperature controlled ion trap using vibrational spectroscopy comprising:
    (1) Providing a composition comprising ions of interest from a chemical sample;
    (2) Introducing said ions into a vacuum tube and passing said ions along the tube at reduced pressure;
    (3) Exposing said ions to a electric or magnetic field at the distil end of said vacuum tube to separate said ions from non-ionic material;
    (4) Directing said ions into said temperature controlled ion trap at very low temperature;
    (5) Exposing said ions in said ion trap to a pulsed complexing gas or gas mixture selected from the group consisting of hydrogen in a $H_2$/helium gas mixture, argon (Ar), neon (Ne), krypton (Kr), xenon (Xe), carbon dioxide ($CO_2$), carbon monoxide (CO), nitrogen ($N_2$), methane ($CH_4$) or sulfur hexafluoride ($SF_6$) for a period sufficient to produce gas-ion adducts to be further analyzed spectrometrically;
    (6) Extracting said gas-ion adducts from naked ions; and
    (7) Conducting mass spectrometric and/or vibrational analysis on said gas-ion adducts which have been extracted pursuant to step.

17. The method according to claim 16 wherein said ions of interest are produced from a chemical sample by electrospray, pulse valve/electron gun, electric impact, chemical ionization, laser ablation, free jet.

18. The method according to claim 17 wherein said ions are produced by electrospray.

19. The method according to claim 16 wherein said vacuum tube is divided into at least two regions of reduced pressure, wherein said pressure is more reduced at the distil end of the vacuum tube.

20. The method according to claim 16 wherein said vacuum tube is divided into at least four regions of increasingly reduced pressure, wherein said pressure is most reduced at the distil end of the vacuum tube.

21. A method for enhancing the resolution of ions of interest prepared from sample compounds in a low temperature controlled ion trap analyzed by vibrational spectroscopy comprising the steps of:
  1. Providing a sample solution or gas mixture comprising a compound to be analyzed;
  2. Converting said compound from step 1 into ions using electrospray, pulse valve/electron gun, electric impact, chemical ionization, laser ablation or free jet methods from said sample solution or gas mixture;
  3. Passing the ions from step 2 at low temperature into a vacuum tube with at least one Rf guide comprising four or more regions of progressively increasing vacuum and propagating the ions (propagated ions) through the regions;
  4. At the distil end of the vacuum tube in step 3 removing non-ions from said ions before introducing said propagated ions into said low temperature ion trap;
  5. Introducing a pulsed complexing gas or gas mixture selected from the group consisting of hydrogen in a hydrogen:helium mixture, argon, neon, krypton, xenon, carbon dioxide, carbon monoxide, nitrogen, methane, and sulfur hexafluoride gas into said ion trap containing ions at approximately ambient (room) temperature to allow the gas to condense in the presence of ions in the ion trap for a period sufficient to form a mixture of gas-ion adducts and non-adduct (naked) ions;
  6. Extracting the gas-ion adducts from naked ions of step 5 by passing the contents of the ion trap into an extractor which performs the extraction;
  7. Introducing the gas-ion adducts obtained from extracting step 6 into a mass spectrometer;
  8. Exposing said gas-ion adducts to mass spectrometry and infrared spectroscopy and optionally, UN and/or visible spectroscopy; and
  9. Obtaining mass spectrometric and vibrational spectra and optionally UV and/or visible spectra for the exposed ions of step 8.

22. The method according to claim 21 wherein said vibrational analysis occurs at a wavelength ranging from about 600-4300 $cm^{-1}$.

23. The method according to claim 21 wherein said vibrational analysis identifies and/or characterizes at least one or more of the following functional groups: C—O in alcohols or esters, N—H in an amine or amide, C=C in an alkene, C=O in aldehydes, ketones, esters or amides, O—H in carboxylic acids, C—H in alkanes, C—H in alkenes, O—H bonds in alcohols, C≡C in alkynes, C≡N in cyano groups and $CO_2$ groups.

* * * * *